United States Patent [19]
Fujita et al.

[11] Patent Number: 5,480,791
[45] Date of Patent: Jan. 2, 1996

[54] METHOD OF DETECTING PHOSPHATASE

[75] Inventors: Satoshi Fujita; Naoto Kagiyama; Masayoshi Momiyama; Yasumitsu Kondo, all of Sapporo, Japan

[73] Assignee: Aisin Seiki Kabushiki Kaisha, Kariya, Japan

[21] Appl. No.: 155,819

[22] Filed: Nov. 23, 1993

[30] Foreign Application Priority Data

Nov. 24, 1992 [JP] Japan .................................... 4-353462
Oct. 7, 1993 [JP] Japan .................................... 5-277499

[51] Int. Cl.$^6$ .............................. C12Q 1/68; C12N 9/16
[52] U.S. Cl. .................................. 435/196; 435/6
[58] Field of Search ......................... 435/6, 196

[56] References Cited

FOREIGN PATENT DOCUMENTS 2115748 10/1972 Germany .
4117619 12/1992 Germany .
2246859 2/1992 United Kingdom .

OTHER PUBLICATIONS

E. J. M. Speel et al., "A Novel Fluorescence Detection Method for in situ Hybridization, Based on the Alkaline Phosphatase–Fast Red Reaction", *The Journal of Histochemistry and Cytochemistry*, vol. 40, No. 9, pp. 1299–1308 (1992).

*The Histochemical Journal*, vol. 24, No. 8, Abstracts of the 9th International Congress of Histochemistry and Cytochemistry (1992).
P. Kupcsulik et al, *Acta Histochemica*, vol. 35, No. 2, (1970) pp. 363–371.
J. Schroeder et al, *Bioengineering*, vol. 5, No. 3–4 (1989) pp. 24–26.
S. West et al, *Analytical Biochemistry*, vol. 190, No. 2, 1 Nov. 1990, New York, pp. 254–248.
H. J. Hoeltke et al, *Analytical Biochemistry*, vol. 207, No. 1, 15 Nov. 1992, New York, pp. 24–31.
West et al., Analytical Biochem. 190:254–258 (1990).
Ziomek et al., J. Histochem. Cytochem. 38(3):437–442 (1990).
Sigma Chem. Co. Catalog (1991) pp. 701–703.

*Primary Examiner*—Stephanie W. Zitomer
*Attorney, Agent, or Firm*—Burns, Doane, Swecker & Mathis

[57] ABSTRACT

An easy operable method of detecting phosphatase which comprises a step for the production of a dye to obtain an azo dye by the reaction of phosphatase in a tissue or cell or on chromosome with a 2'-naphthol AS phosphate, specifically, 3-hydroxy- N-2'-biphenyl-2-naphthalenecarboxamide phosphate ester, followed by the reaction between the dephosphorylated 2'-naphthol AS compound with a diazonium salt; an excitation step for the irradiation of excited light to the azo dye; and a detection step for the detection of fluorescence which is emitted upon irradiation of the excited light. The fluorescence is intense and lasts for a long time.

4 Claims, 17 Drawing Sheets

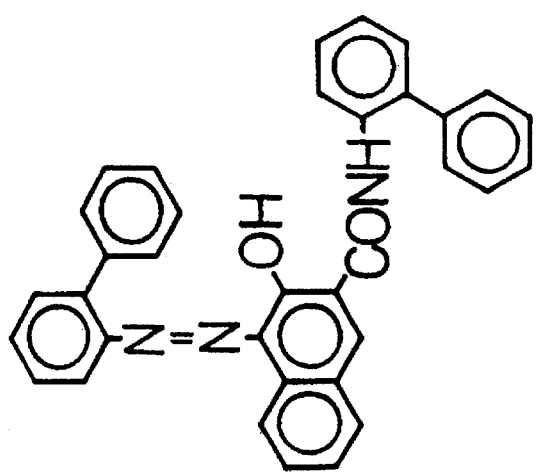
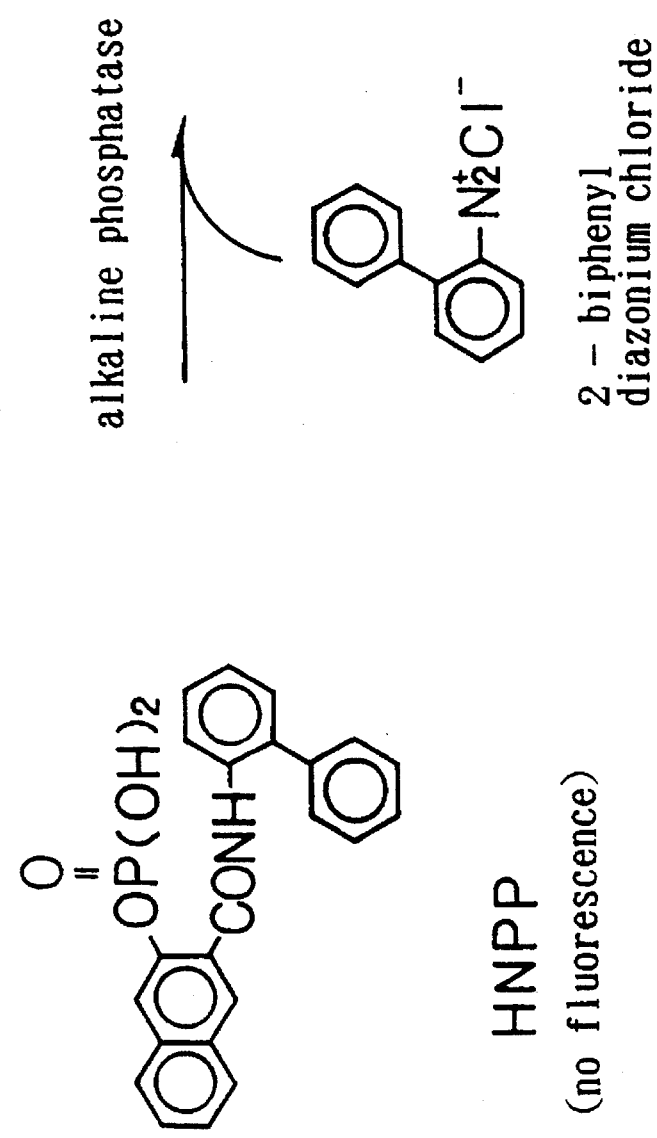
FIG. 1

FIG. 25

| sample No. | $X_3$ | λex | λem | Specific FL ※ | diffusion a) |
|---|---|---|---|---|---|
| present invention 1 | Ph-Ph (phenyl substituent) | 321 367nm | 474 565nm | 6.3 | ○ |
| present invention 2 | CH₃-Ph | 326 371 | 477 558 | 19.4 | ○ |
| comparative 3 | Ph-Cl | 322 368 | 472 558 | 0.6 | × |
| comparative 4 | Ph, OCH₃ substituted | 324 370 | 472 595 | 1.1 | △ |
| comparative 5 | CH₃-Ph-Br | 370 | 570 | 0.3 | △ |

※ strength of fluorescent light compared with sample 6 a) ○ : less diffusion
△ : intermediate
× : more diffusion

FIG. 27

| | Sample No. | X₃ | λex (nm) | λem (nm) | Specific FL ※ | diffusion a) |
|---|---|---|---|---|---|---|
| present invention | 6 | Ph-⬡- | 358 | 555 | 1 | △ |
| | 7 | CH₃-⬡- | 557 | 580 | 0.7 | △ |
| comparative samples | 8 | -⬡-Cl | 365 | 560 | 0.9 | × |
| | 9 | -⬡(Ph)(OCH₃) | 590 | 595 | 1.6 | △ |
| | 10 | CH₃-⬡-Br | 297 / 317 | 476 / 555 | 1.5 | △ |

※ strength of fluorescent light compared with sample 6 a) ○ : less diffusion
△ : intermediate
× : more diffusion

METHOD OF DETECTING PHOSPHATASE

FIELD OF THE INVENTION

The present invention relates to a fluorescent substance for the detection of phosphatase, which is very useful in, for example, the case where chromosome map is prepared by the use of phosphatase for genome analysis involving in-situ hybridization and the case where acid phosphatase and alkaline phosphatase in tissues or cells are detected.

DESCRIPTION OF THE PRIOR ART

For the in-siti hybridization of RNA or chromosomal DNA in tissues or cells or for the detection of specific antigens, immunofluorescence is often utilized in which an RNA or chromosomal DNA-bound antigen is linked to an antibody which is bound to a fluorescent substance, and detection is made of the fluorescence of the fluorescent substance. The number of the fluorescent substance which is allowed to be bound to a single antibody is, however, only several to several dozens of molecules, for which the sensitivity is restricted accordingly. Such immunofluorescence includes, for instance, a method which utilizes an FITC-bound antibody.

In order to accomplish a great improvement of the sensitivity, it is desired to link an enzyme to an antibody by enzyme antibody technique. Here the enzyme antibody technique is for the detection of a specific antigen that has been bound to RNA or chromosomal DNA, which comprises linking of an enzymes-bound antibody to an antigen which have been bound to RNA or chromosomal DNA, followed by the reaction of a fluorescent substrate with the enzyme to produce a fluorescent substance, and detection of the fluorescence given off by the fluorescent substance.

There is no limit to be placed on a decomposition reaction of a fluorescent substrates with an enzyme. Therefore, for example, a decomposition reaction of a fluorescent substrate with alkaline phosphatase allows the reaction of about 100,000 molecules of the fluorescent substrate per minute. This enables a 10,000-fold or more improvement of the fluorescent sensitivity as compared with the performance of the above-mentioned immunofluorescence technique.

Immunofluorescence technique which utilizes the above-mentioned FITC-bound antibody, however, undergo rapid fading of the excited light, and the fluorescence disappears in several seconds in a usual indoor lighting environment.

Accordingly the fluorescence must be detected immediately after its emission. Further the procedures must be followed in a dark room, resulting in a poor working efficiency. In addition an expensive laser microscope is required for the observation of the exited light, leading to a less general-purpose technique.

Furthermore the fluorescence due to the FITC-bound antibody has a poor sensitivity and resolution. This presents a problem that superposition by image processing becomes necessary for the determination of the location of a certain base sequence site of the RNA or chromosomal DNA. That is, the emitted DNA on the chromosome due to the FITC-bound antibody must be superposed on the image entire chromosome.

Under these circumstance, with an aim to solve those problems, E. J. M. Speel, et al. tried an enzyme antibody technique for the detection of fluorescence due to the use of Naphthol-AS/MX-phosphate, a commercially available fluorescent substrate and Fast Red TR which is an azo dye.

This process aims to improve the ability of a fluorescent substance to deposit on tissues or chromosomes through coupling of Naphthol-AS/MX-phosphate and Fast Red TR in in-situ hybridization (The Histochemical Journal, vol. 24, p. 562, 1992; gist of the 9th International Histochemistry Conference).

The process according to E. J. M. Speel et al. confirmed the delayed fading due to the improved deposition ability as compared with the prior art FITC immunofluorescence technique mentioned above.

Nevertheless, the above process according to E. J. M. Speel, et al. fails to provide a better sensitivity than the above-mentioned FITC immunofluorescence technique of the prior art, and thus it has served mere to partially solve the problems. Thus, in view of these drawbacks of the prior art, the present invention intends to provide an easily operable method of detecting phosphatase which enables the emission of an intense fluorescence over a long period of time.

SUMMARY OF THE INVENTION

The present invention aims to provide an easily operable method of detecting phosphatase which enables the emission of an intense fluorescence over a long period of time.

An easy operable method of detecting phosphatase which comprises a step for the production of a dye to obtain an azo dye by the reaction of phosphatase in a tissue or cell or on chromosome with a 2'-naphthol AS phosphate, e.g. 3-hydroxy- N-2'-biphenyl-2-naphthalenecarboxamide phosphate ester, followed by the reaction between the 2'-naphthol AS phosphate with a diazonium salt; an excitation step for the irradiation of excited light to the azo dye; and a detection step for the detection of fluorescence which is emitted upon irradiation of the excited light. The fluorescence is intense and lasts for a long time.

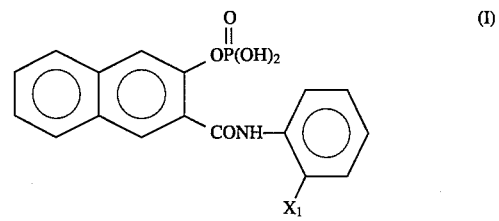

(I)

BRIEF DESCRIPTION OF THE DRAWINGS

The file of this patent contains twenty drawings executed in color. Copies of this patent with the color drawings will be provided by the U.S. Patent Trademark Office upon request and payment of the necessary fee.

FIG. 1 illustrates the reaction between HNPP(3-hydroxy-N-2'-biphenyl-2-naphthalenecarboxamide phosphate ester) and 2-biphenyl diazonium chloride according to the present invention;

FIG. 8 is a photomicrograph (magnification:×100) of a mouse kidney tissue which shows the detection of phosphatase by the use of HNPP and a diazonium salt (4-chloro-2-toluene diazonium chloride) in Example 2;

FIG. 25 illustrates the degree of diffusion of phosphatase in a frozen mouse kidney tissue and the $\lambda_{ex}$ and $\lambda_{em}$ values of azo dyes when HNPP and various diazonium salts in Example 12 were used;

FIG. 27 illustrates the degree of diffusion of phosphatase in a frozen mouse kidney tissue and the $\lambda_{ex}$ and $\lambda_{em}$ values of azo dyes when HMPNP and various diazonium salts in Example 13 were used.

DETAILED DESCRIPTION OF THE INVENTION

The present invention is a method of detecting phosphatase, which comprises a step for the production of a dye to obtain an azo dye by the reaction of phosphatase with 2'-naphthol AS phosphate represented by the general formula I below, for the coupling between the 2'-naphthol AS phosphate and a diazonium salt; an excitation step for the irradiation of excited light to the above azo dye; and a detection step for the detection of fluorescence which is emitted upon irradiation of the excited light, characterized in that the 2'-substituent X1 on the above 2'-naphthol AS phosphate is any one of phenyl group, methyl group, isopropyl group and methoxy group.

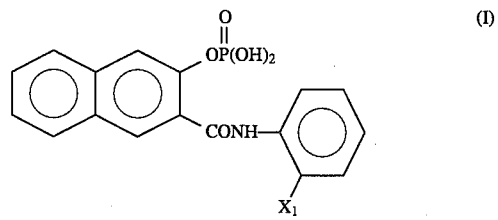

Figure 2:
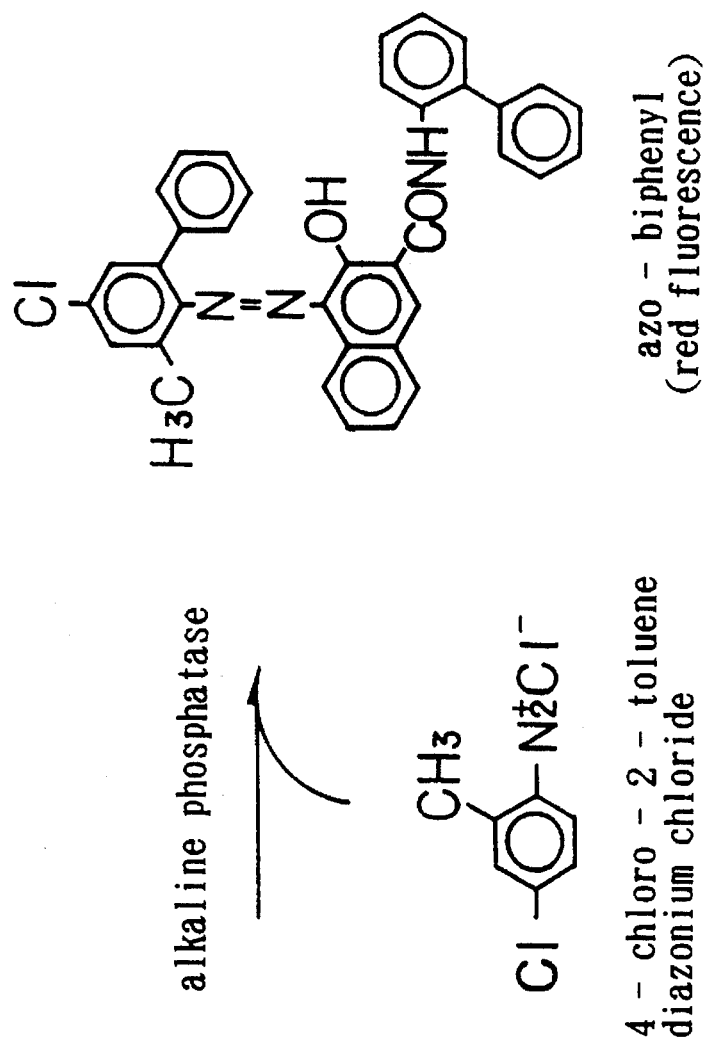
FIG. 2 illustrates the reaction between HNPP(3-hydroxy-N-2'-biphenyl-2-naphthalenecarboxamide phosphate ester) and 4-chloro-2-toluene diazonium chloride according to the present invention.
Figure 3:
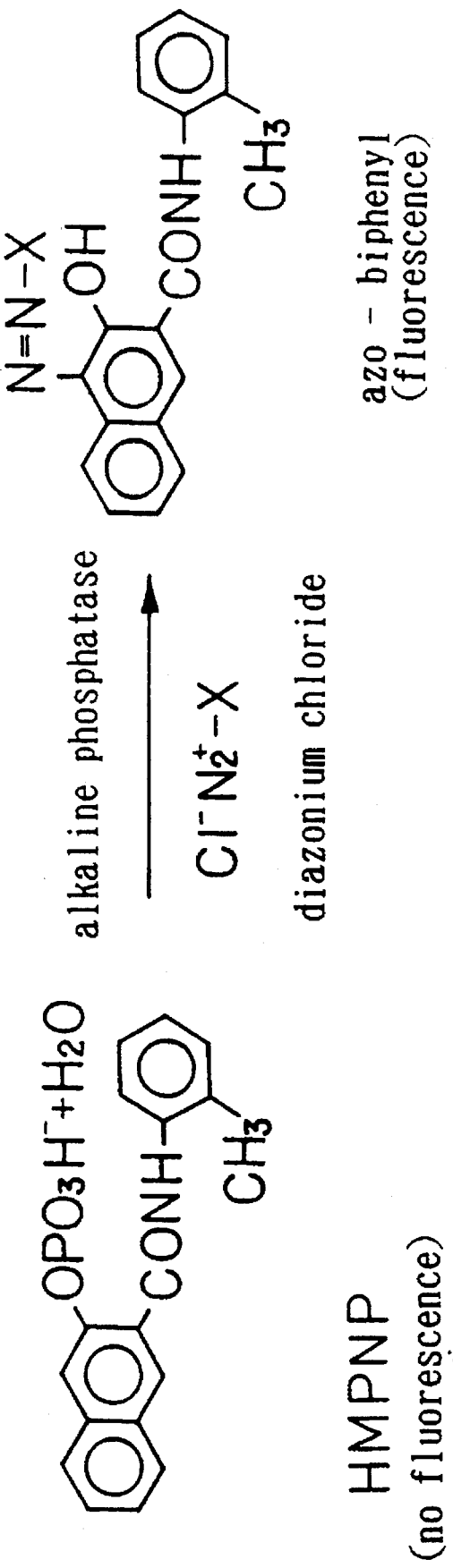

According to the present invention, an azo dye is produced by the above-mentioned coupling reaction between the naphthalene ring of the above 2'-naphthol AS phosphate and the above diazonium salt in the presence of phosphatase (see FIGS. 1–3).

This azo dye is the so-called coupling product between the dephosphorylated form of the above-mentioned 2'-naphthol AS phosphate and a diazonium salt. Furthermore, this azo dye is a stable compound and further a fluorescent substance which gives off an intense fluorescence.

Here the above 2'-naphthol AS phosphate means a compound of the formula I wherein the above substituent $X_1$ such as phenyl group is located at 2'-position (ortho-position) alone and no substituent is present at 3' and 5'-positions (meta-positions) and 4'-position (para-position).

For example, the 2'-naphthol AS phosphate which has a phenyl group at the 2'-position of the above benzene ring is 3-hydroxy-N-2'-biphenyl-2-naphthalenecarboxamide phosphate ester (hereunder referred to as HNPP). Its chemical formula is shown by the formula II below.

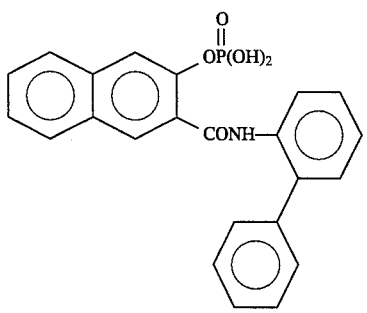

(II)

As illustrated in FIG. 1, HNPP reacts with a diazonium salt, e.g., 2-biphenyl diazonium chloride in the presence of phosphatase to produce a chromophoric azo dye.

Further, as FIG. 2 demonstrates, HNPP reacts with 4-chloro-2-toluene diazonium chloride, a chromophoric diazonium salt, to produce a chromophoric azo dye.

Here, as an example, 2'-naphthol AS phosphate having a methyl group at the 2'-position of the above benzene ring is 3-hydroxy-N-2'-methylphenyl-2naphthalenecarboxamide phosphate ester(hereunder referred to as HMPNP). The chemical structure thereof is shown in formula III below.

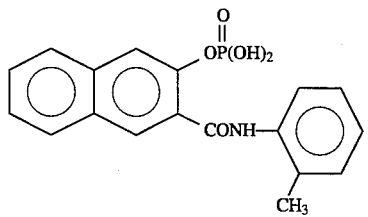

(III)

As is illustrated in FIG. 3, HMPNP reacts with a diazonium chloride in the presence of phosphatase to produce a chromophoric azo dye.

The foregoing applies to the other 2'-naphthol AS compounds as well, and the listing of their names is omitted.

In addition, the above-mentioned 2'-naphthol AS phosphate may include those represented by the formula IV below which has a substituent $X_2$ at the 7-position of the naphthalene ring.

The above substituent X, includes H, Br, phenyl group ($C_6H_5$), methyl group ($CH_3$), isopropyl group ($CH_2(CH_3)$ $CH_3$), etc.

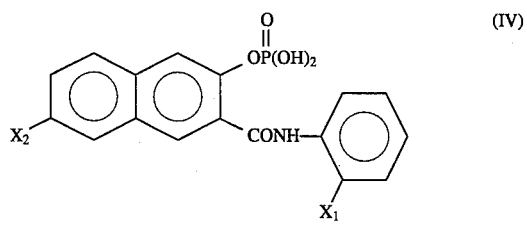

(IV)

In general the above-mentioned phosphatase includes phosphatase which is present in tissues or cells, and further phosphatase labelled with a nucleic acid probe. The above-mentioned tissue includes, e.g., kidney or liver tissue.

The above-mentioned chromosome may be an endogenous one in a tissue or an external one taken out from a tissue.

In addition, the above phosphatase is present on, for example, a nucleic acid probe. This nucleic acid probe may be subjected to hybridization with RNA or chromosomal DNA in tissues or cells.

That is, first a nucleic acid probe labelled with phosphatase is hybridized with a certain base sequence site of RNA or on chromosomal DNA in a tissue or cell. Then removal is made of the portion of the above-mentioned nucleic acid probe which has not taken part in the hybridization with the certain base sequence site.

Thereafter the above-mentioned phosphatase is reacted with a 2'-naphthol AS phosphate for the coupling between the 2'-naphthol AS phosphate and a diazonium salt, resulting in the production of an azo dye. The subsequent irradiation of an excited light to the above-mentioned azo dye causes emission of fluorescence from the azo dye which is to be detected.

Thus the above-mentioned certain base sequence site of RNA or chromosomal DNA my be detected.

On the other hand, prior to the linking of the above nucleic acid probe to the above phosphatase, it is usual to bond an antibody to the phosphatase, and an antigen to the nucleic acid probe first. And after that, the antibody and the antigen are subjected to the reaction.

The phosphatase available for use according to the present invention my be either alkaline phosphatase or acid phosphatase.

The above-mentioned diazonium salt may be one or more which is selected from the group consisting of 2-biphenyl diazonium chloride, 4-methoxy-2-biphenyl diazonium chloride, 3-biphenyl diazonium chloride, 4-methoxy-3-biphenyl diazonium chloride, 2-toluene diazonium chloride, 4-chloro-2-toluene diazonium chloride, 3-bromo-6-toluene diazonium chloride, 3-bromo-4-toluene diazonium chloride, 2-methoxybenzene diazonium chloride, 2,4-dimethoxy benzene diazonium chloride, 3-chloro-4,6-dimethoxy benzene diazonium chloride, 2-bromobenzene diazonium chloride, 3-acetamidobenzene diazonium chloride, naphthalene diazonium chloride, 3-hydroxy-2-naphthalene diazonium chloride, 2-anthracene diazonium chloride, 2',4'-dimethoxy-4-stilbene diazonium chloride, benzothiazole diazonium chloride, 5-diethylaminosulfonyl-2-methoxybenzene diazonium chloride, 4-methoxy-2-nitrobenzene diazonium chloride, 2-methoxy-4-nitrobenzene diazonium salt, p-nitrobenzene diazonium tetrafluoroborate, 2-methoxy-5-chlorobenzene diazonium chloride and 2-methoxy-3-dibenzofuran diazonium salt.

According to the detection method of the present invention, a 2'-naphthol AS phosphate is bound to a diazonium salt in the presence of phosphatase to produce an azo dye.

This azo dye has a stable structure and emits a more intense fluorescence than the fluorescent substances of the prior art. And the fluorescence time is approximately 30 minutes or more, and thus the fluorescence lasts for a long time. Therefore phosphatase may be detected at a high sensitivity; for example, high sensitive detection of RNA or chromosomal DNA in tissues or cells is possible.

Particularly the sensitivity may be further improved when the diazonium salt is a biphenyl diazonium chloride type of diazonium salt.

Accordingly the detection method of the present invention may be carried out under the usual lighting, which contributes to an increased working efficiency. Furthermore there is no need to effect the fluorescence detection in a dark room.

The foregoing effects are supposed to result from the fact that the azo dyes referred to above have a stable structure and excellent ability to deposit on cells, tissues or chromosomes.

Additionally, as the fluorescence undergoes little fading even upon exposure to an intense excited light source, the method my by applied to not only the characterization but also the quantitative analysis of phosphatase.

Further, the 2'-naphthol AS phosphates do not emit fluorescence prior to their reaction with phosphatase, so it is easy to detect a luminescent signal in the reaction solution thereby confirming the presence or absence of phosphatase.

Moreover the practice of the method of detecting phosphatase according to the present invention after the above-mentioned hybridization between RNA or chromosomal DNA and a nucleic acid probe presents information useful for the determination of the location of a certain base sequence site of the RNA or chromosoml DNA.

Also, for the determination of the location of a certain base sequence site of the RNA or chromosomal DNA, both the certain base sequence and the entire chromosome my be photographed on the same image. This makes the image processing easy. In addition, the diffusion of the excited light is little enough to provide a vivid image.

Additionally, the excited light may be observed with an ordinary fluorescence microscope.

Meanwhile, the choice of the type of diazonium salt enables the change of the wave length of the fluorescent signal. For this, the present invention my be applied to multi-color fluorescence detection systems which employ several kinds of nucleic acid probes as well.

For example, HNPP and 4-chloro-2-toluene diazonium chloride are used when FITC probe is used in combination therewith, while HNPP and p-nitrobenzene diazonium tetrafluoroborate are used when TRITC probe is used in combination therewith. Here, a red color is developed in the former case, whereas a yellow color in the latter.

The thus produced fluorescent azo dyes emit a more intense fluorescence than the fluorescent substances of the prior art, and further are substances which have excellent ability to deposit on tissues or chromosomes, and therefore with them a higher sensitive detection of RNA or chromosomal DNA in tissues or cells is possible. Therefore, according to the-present invention, it is possible to detect the RNA in a tissue or cell or chromosomal DNA which has been label led with phosphatase and subjected to in-situ hybridization, at a higher sensitivity than before.

As mentioned above, an intense fluorescence may be emitted for a long time according to the present invention which therefore presents an easy operable method of detecting phosphatase.

EXAMPLES

Example 1

In this example, phosphatase in the frozen tissue preparation of mouse kidney was reacted with the above-mentioned HNPP, a 2'-naphthol AS phosphate, to which was bound 2-biphenyl diazonium chloride to yield an azo dye. Excited light was irradiated to the azo dye and the fluorescence which was emitted by the irradiation of the excited light was detected.

A detailed explanation will be given regarding this.
1) Preparation of 2-biphenyl diazonium chloride First, 500 mg of o-aminobiphenyl was dissolved in 2.4 ml of 13.6% hydrochloric acid (4 molar equivalents), and the resulting solution was subjected to ultrasonic treatment for 10 minutes and then kept at the freezing point. To the solution at the freezing point was added dropwise 0.8 ml of a 25 % aqueous solution of sodium nitrite (1 molar equivalent) slowly while stirring. After the addition, the mixture was stirred at the freezing point for 2 hours, followed by addition of 0. 6 ml of saturated zinc chloride while stirring at the freezing point. This caused precipitation of zinc chloride double salt of diazonium chloride.

Then, the mixture was allowed to stand at 0° C. for 2 hours while stirring sometimes. Next, it was filtered by suction and washed with cold ether, followed by air drying. Thus there was produced 650 mg of zinc chloride double salt of 2-biphenyl diazonium chloride.
2) Preparation :of reaction solution Thereafter, a substrate solution, which was prepared dissolving HNPP in a Tris-HCl buffer solution (Tris-HCl 100 mM, NaCl 1 100 mM, $MgCl_2$ 50 mM) to a concentration of 100 μg/ml, and a diazonium solution, which was prepared by,dissolving the above-mentioned zinc chloride double sat of 2-biphenyl diazonium chloride in dimethylformamide to a concentration of 250 μg/ml, were mixed to prepare a reaction solution.
3) Detection of phosphatase on frozen tissue preparation of mouse kidney Kidneys were extracted from a mouse and then frozen at −15° C., after which a frozen tissue slice approximately 10 micron thick was prepared by cutting off therefrom. This frozen tissue slice was then immersed into acetone at −15° C. for more than several hours, thereafter it was placed in 4% paraformamide and fixed on an slide glass for 20 minutes, followed by washing with a phosphate buffer solution (NaCl 130 mM, $Na_2HPO_4$ 7 mM, $NaH_2PO_4$ 30 mM) three times each for 5 minutes and storage in a phosphate buffer solution at 4° C.

Then, the slide glass with the above-mentioned frozen tissue slice thereon was immersed into the above-mentioned reaction solution for an approximately 5 minutes' reaction at room temperature. After the reaction, the slide glass was washed with water three times, and, after the water was well drained off, glycerol was added dropwise to the slide glass for encapsulation.

Figure 4:
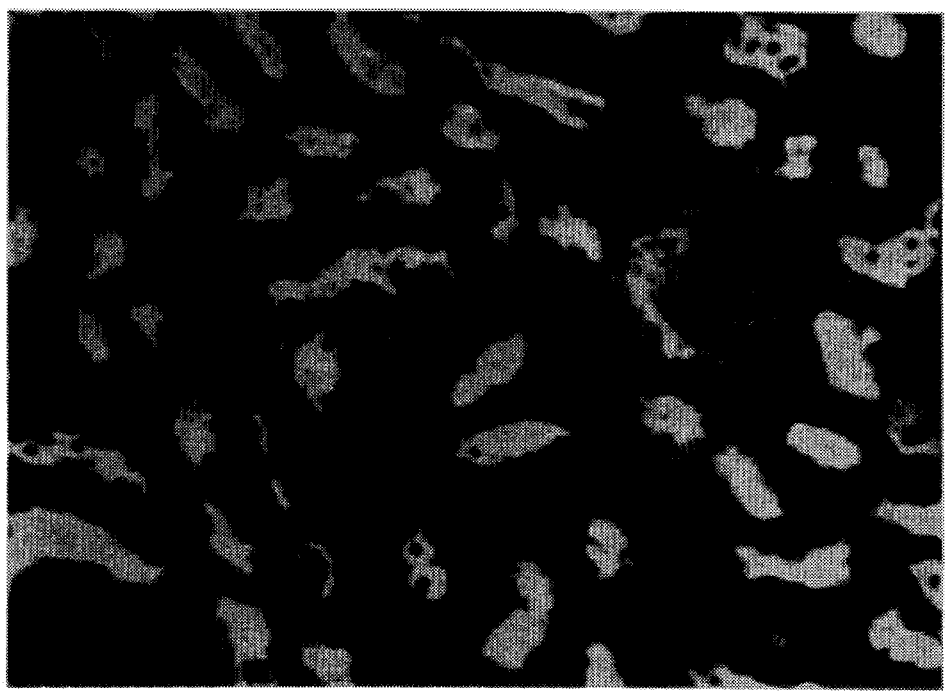
FIG. 4 is a photomicrograph (magnification:×100) of a mouse kidney tissue which shows the detection of phosphatase by the use of HNPP and a diazonium salt (2-biphenyl diazonium chloride) in Example 1.

Then, the observation of the fluorescent signal emitted from the tissue slice on the slide glass was carried under a fluorescence microscope. As a result, as illustrated in FIG. 4 (photograph, microscope magnification:×100: aperture: open, exposure time: 30 seconds), an intense red fluorescence was detected. Example 2

In this example, phosphatase in the frozen mouse kidney tissue preparation was detected in the same manner as in Example 1 except that each of the following diazonium salts was used instead of the 2-biphenyl diazonium chloride in Example 1, in combination with the above-mentioned HNPP.

That is, the diazonium salts used in this example include the following:

4-methoxy-2-biphenyl diazonium chloride, 3-biphenyl diazonium chloride, 4-methoxy-3-biphenyl diazonium chloride, 2-toluene diazonium chloride, 4-chloro-2-toluene diazonium chloride, 3-bromo-6-toluene diazonium chloride, 3-bromo-4-toluene diazonium chloride, 2-methoxybenzene diazonium chloride, 2,4-dimethoxybenzene diazonium chloride, 3-chloro-4,6-dimethoxybenzene diazonium chloride, 2-bromobenzene diazonium chloride, 3-acetamidobenzene diazonium chloride, naphthalene diazonium chloride, 3-hydroxy-2-naphthalene diazonium chloride, 2-anthracene diazonium chloride, 2',4'-dimethoxy-4-stilbene diazonium chloride, benzothiazole diazonium chloride, 5-diethylaminosulfonyl-2-methoxybenzene diazonium chloride, 4-methoxy-2-nitrobenzene diazonium chloride, methoxy-4-nitrobenzene diazonium salt, p-nitrobenzene diazonium tetrafluoroborate, 2-methoxy-5-chlorobenzene diazonium chloride and 2-methoxy-3-dibenzofuran diazonium chloride.

All the results were photographed under entirely the same conditions (microscope magnification:×100; aperture: open, exposure time: 30 seconds), an extremely intense red fluorescence was detected in the same manner as in Example 1.

FIGS. 5–15 show the results of the above detection of phosphatase when the various diazonium salts were used.

That is, FIGS. 5–9 reflect the cases of the use of 4-methoxy-2-biphenyl diazonium chloride, 3-biphenyl diazonium chloride, 4-methoxy-3-biphenyl diazonium chloride, 4-chloro-2-toluene diazonium chloride and 2-toluene diazonium chloride, respectively.

Also, in the same manner, FIGS. 10–15 reflect the cases of the use of 3-bromo-6-toluene diazonium chloride, 3-bromo-4-toluene diazonium chloride, 2-methoxybenzene diazonium chloride, 2, 4-dimethoxybenzene diazonium chloride, benzothiazole diazonium chloride and 2-methoxy-3dibenzofuran diazonium chloride, respectively.

As shown in the above respective figures, an extremely intense red fluorescence was detected at each of the locations of phosphatase.

Figure 5:
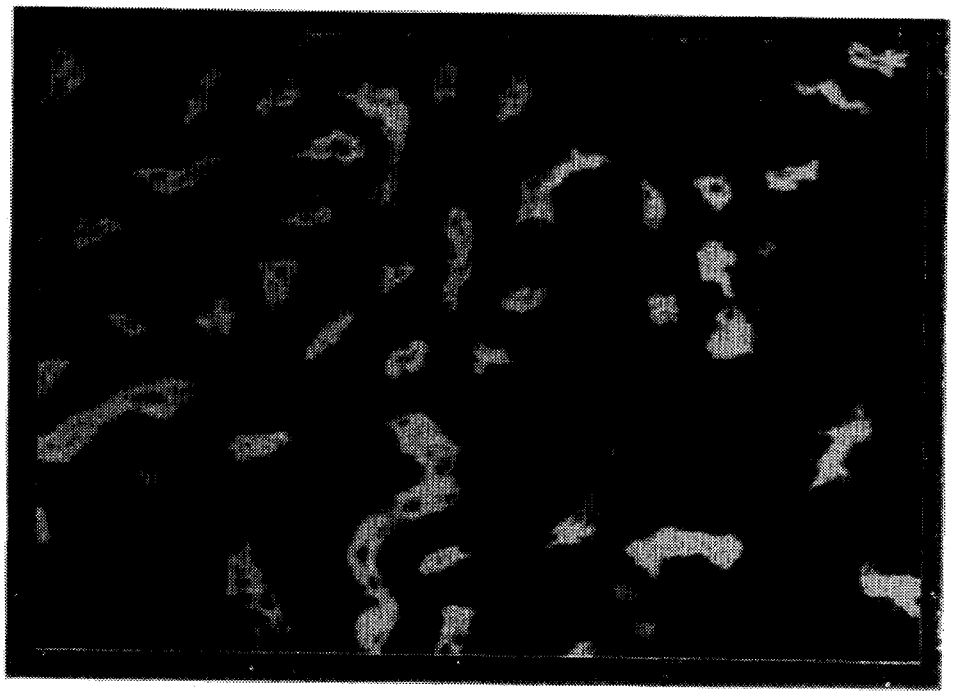
FIG. 5 is a photomicro graph (magnification:×100) of a mouse kidney tissue which shows the detection of phosphatase by the use of HNPP and a diazonium salt (4-methoxy-2-biphenyl diazonium chloride) in Example 2.
Figure 6:
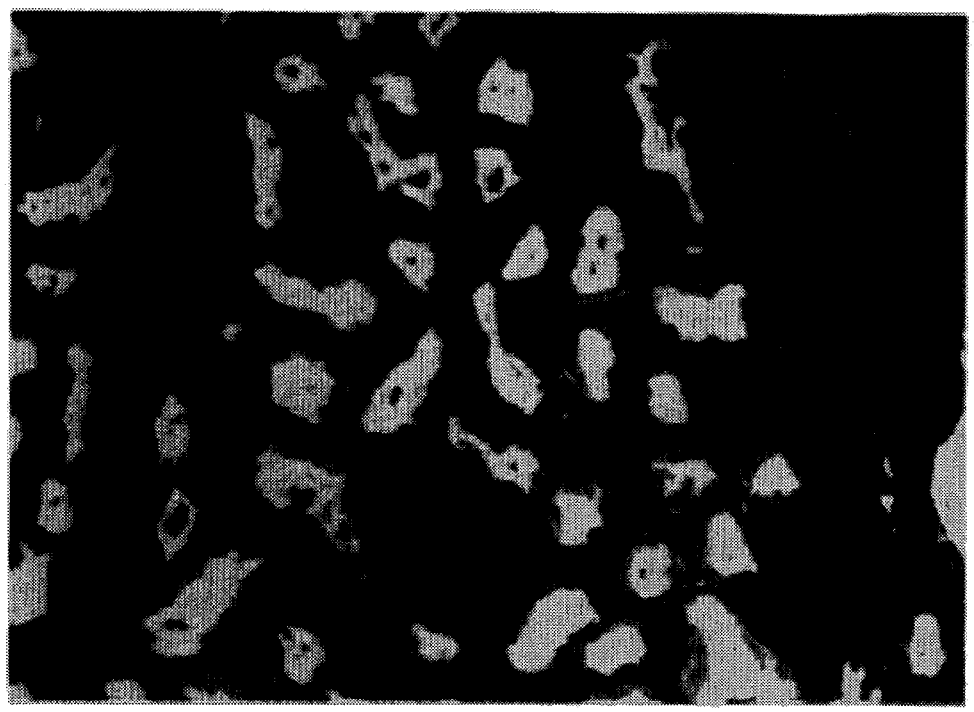
FIG. 6 is a photomicrograph (magnification:×100) of a mouse kidney tissue which shows the detection of phosphatase by the use of HNPP and a diazonium salt (3-biphenyl diazonium chloride) in Example 2.
Figure 7:
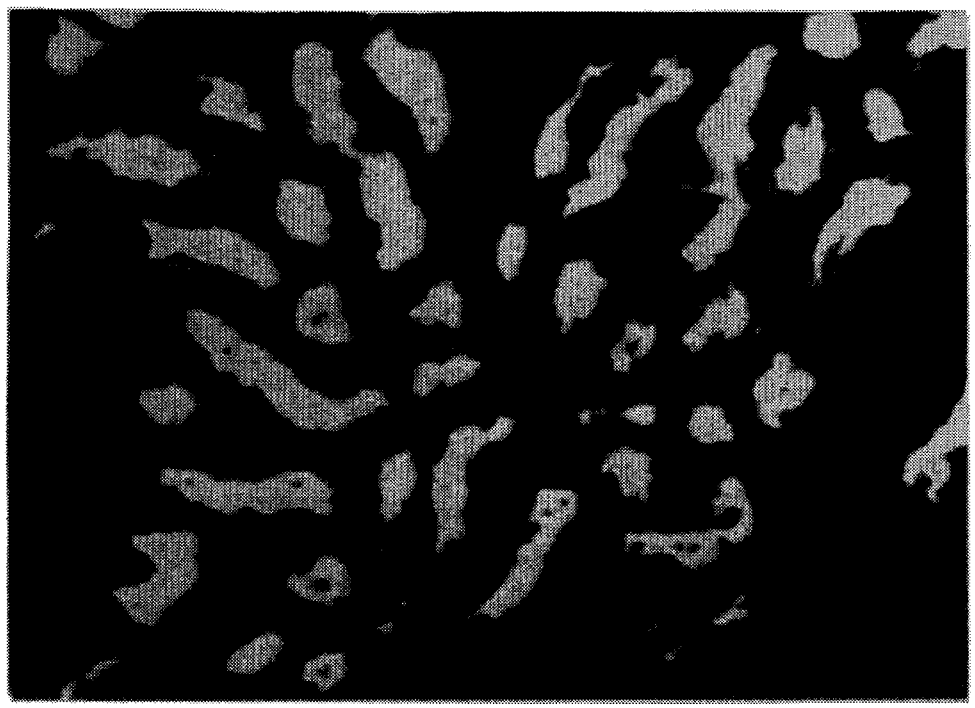
FIG. 7 is a photomicrograph (magnification:×100) of a mouse kidney tissue which shows the detection of phosphatase by the use of HNPP and a diazonium salt (4-methoxy-3-biphenyl diazonium chloride) in Example 2.
Figure 8:
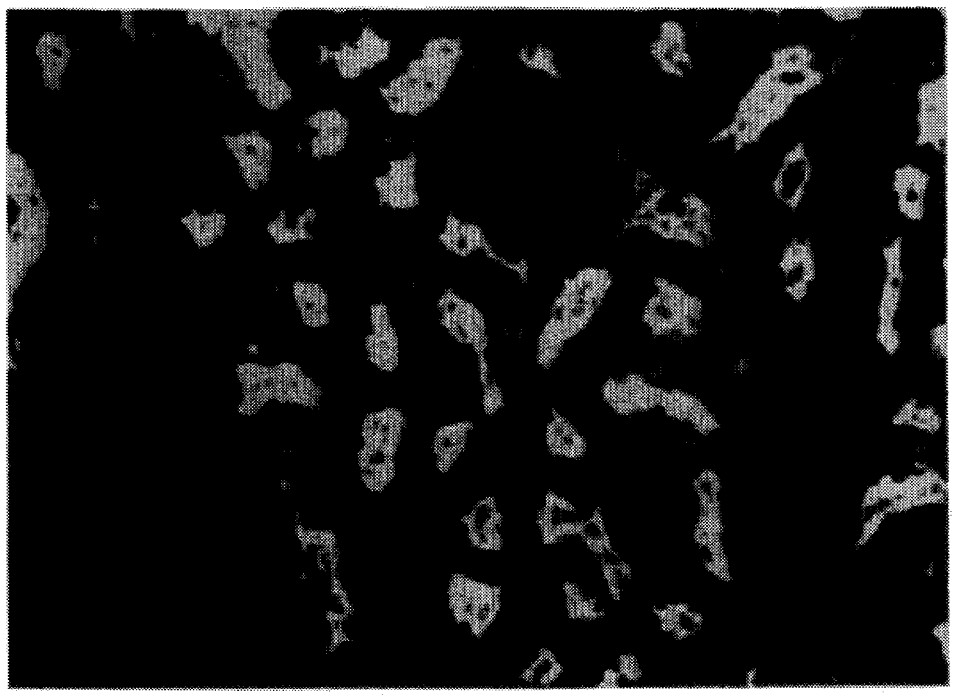
FIG. 8 illustrates the reaction between HMPNP(3hydroxy-N-2'-methylphenyl-2-naphthalenecarboxamide phosphate ester) and a diazonium salt according to the present invention.
Figure 9:
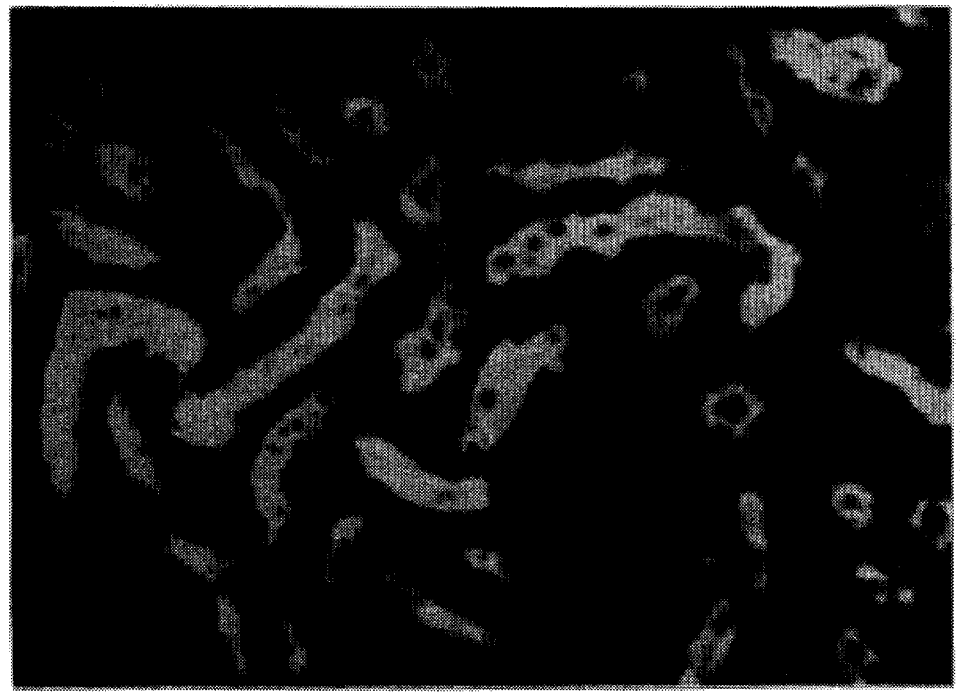
FIG. 9 is a photomicrograph (magnification:×100) of a mouse kidney tissue which shows the detection of phosphatase by the use of HNPP and a diazonium salt (2-toluene diazonium chloride) in Example 2.
Figure 10:
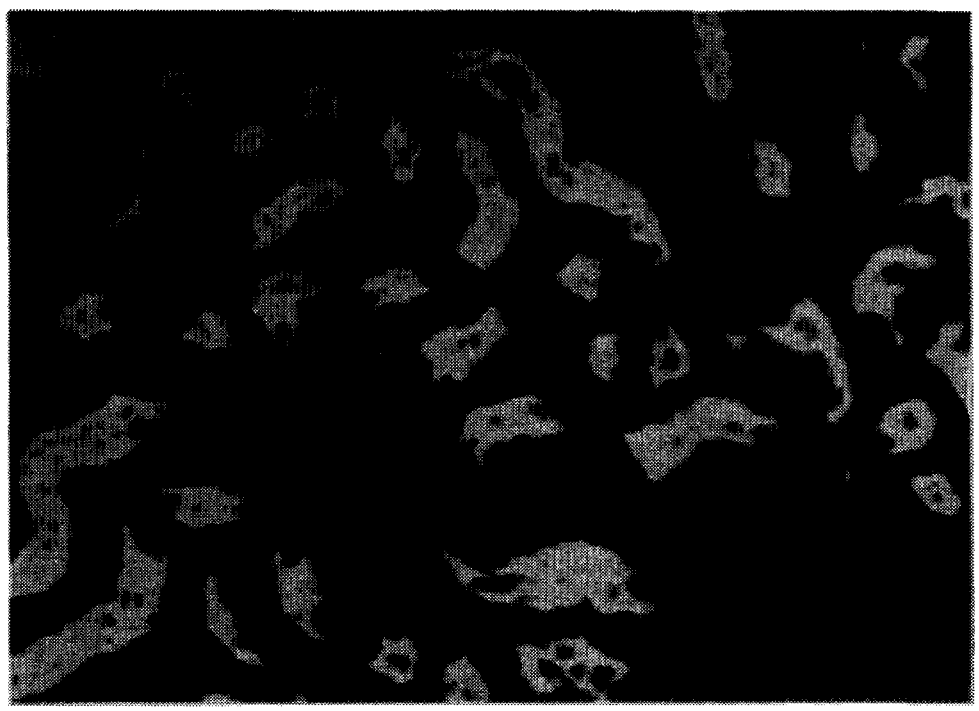
FIG. 10 is a photomicrograph (magnification:×100) of a mouse kidney tissue which shows the detection of phosphatase by the use of HNPP and a diazonium salt (3-bromo-6-toluene diazonium chloride) in Example 2.
Figure 11:
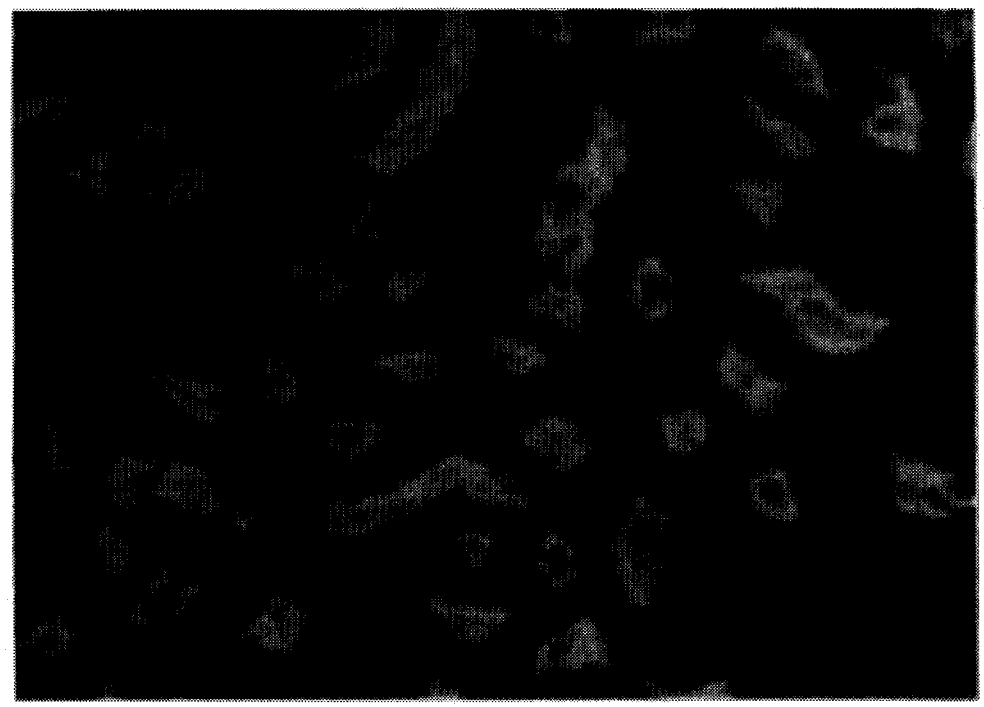
FIG. 11 is a photomicrograph (magnification:×100) of a mouse kidney tissue which shows the detection of phosphatase by the use of HNPP and a diazonium salt (3-bromo-4-toluene diazonium chloride) in Example 2.
Figure 12:
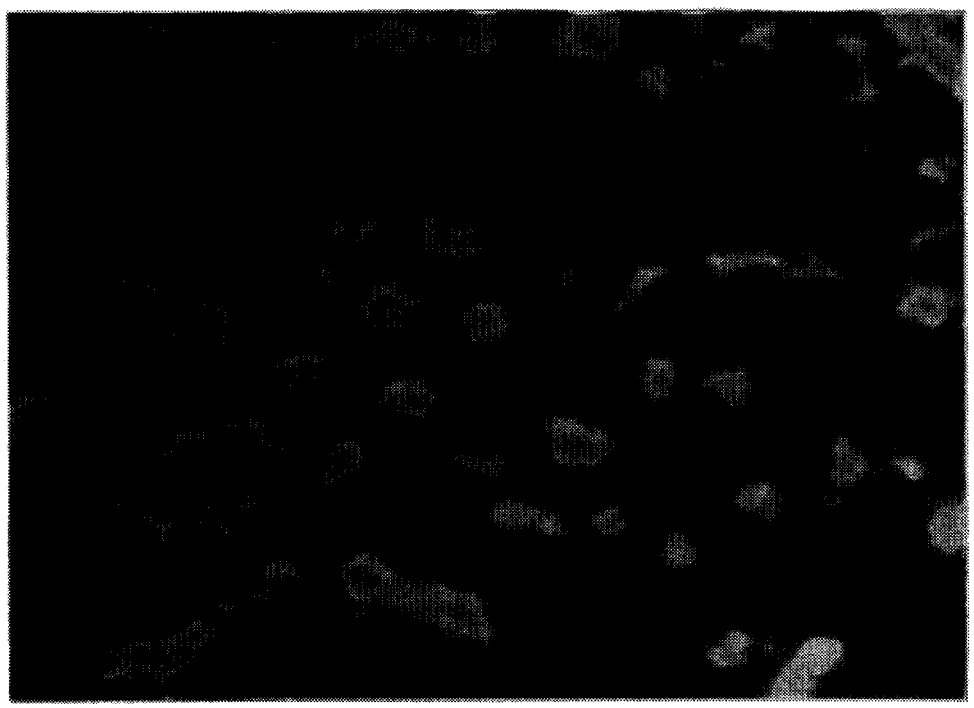
FIG. 12 is a photomicrograph (magnification:×100) of a mouse kidney tissue which shows the detection of phosphatase by the use of HNPP and a diazonium salt (2-methoxybenzene diazonium chloride) in Example 2.
Figure 13:
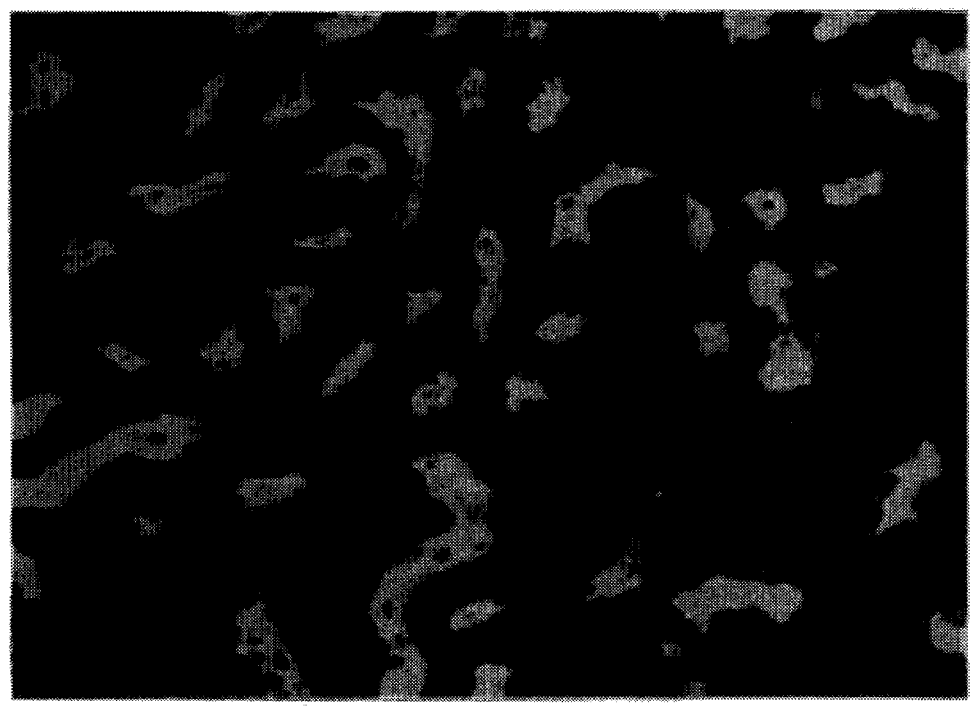
FIG. 13 is a photomicrograph (magnification:×100) of a mouse kidney tissue which shows the detection of phosphatase by the use of HNPP and a diazonium salt (2,4-dimethoxybenzene diazonium chloride) in Example 2.
Figure 14:
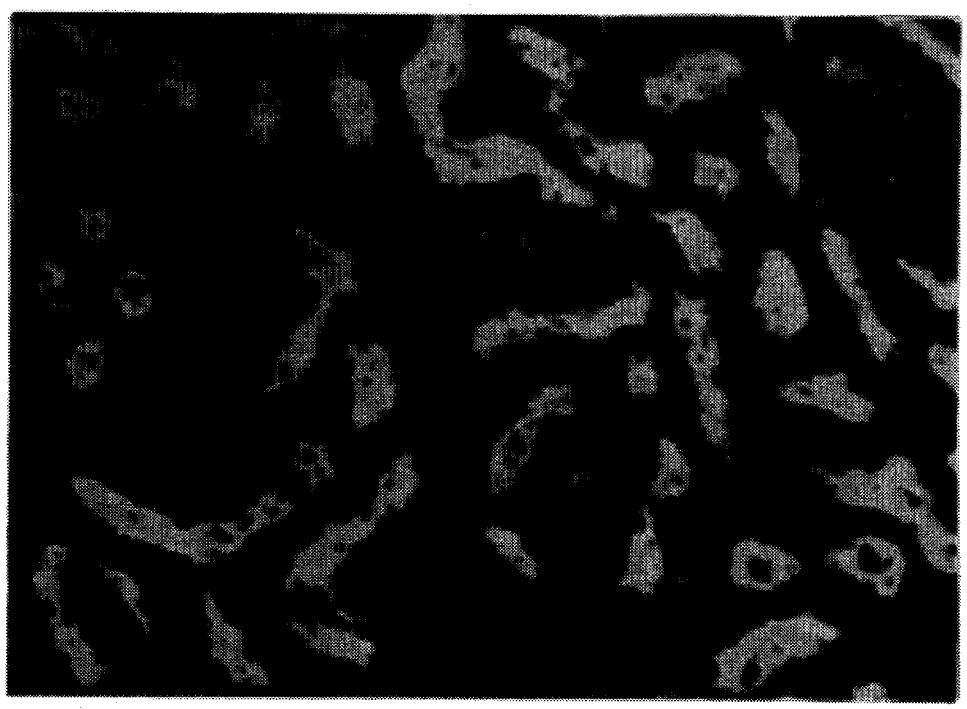
FIG. 14 is a photomicrograph (magnification:×100) of a mouse kidney tissue which shows the detection of phosphatase by the use of HNPP and a diazonium salt (benzothiazole diazonium chloride) in Example 2.
Figure 15:
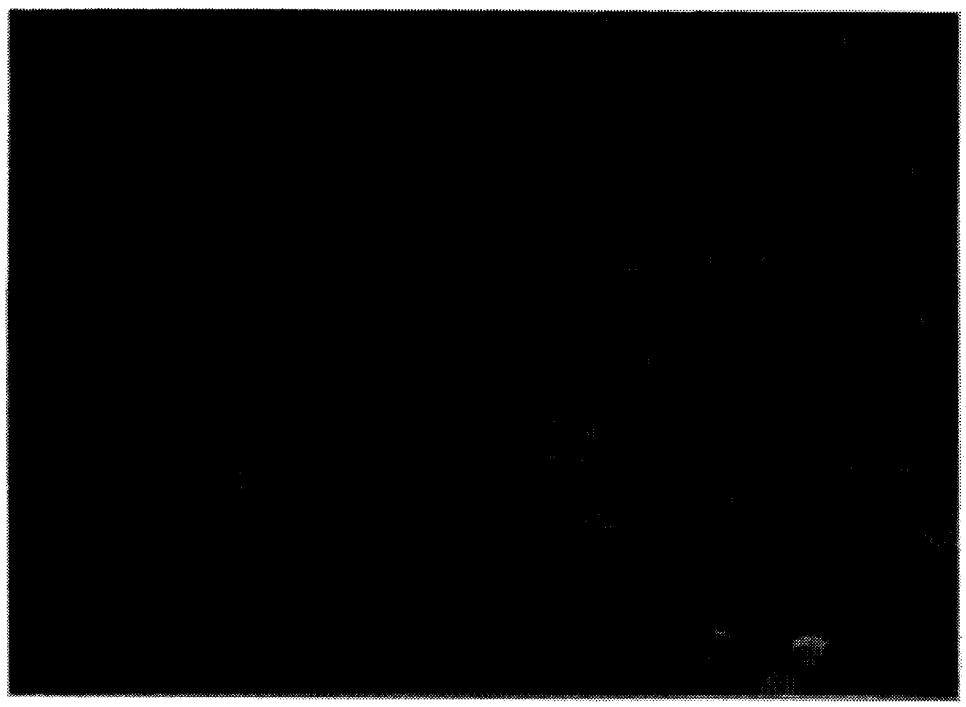
FIG. 15 is a photomicrograph (magnification:×100) of a mouse kidney tissue which shows the detection of phosphatase by the use of HNPP and a diazonium salt (2-methoxy-3-dibenzofuran diazonium chloride) in Example 2.

Notable difference is hard to be reproduced in the photographs, nevertheless, as FIGS. 5–7 show, there is provided faint background which contributes to the particularly easy decision when a biphenyl diazonium chloride is employed as the diazonium salt.

Example 3

In this example, phosphatase in the frozen mouse kidney tissue was detected. For this, a reaction solution was prepared by using HNPP and Fast Red B (green) (product of SIGMA Co. ) (2-methoxy-4-nitrobenzene diazonium chloride) instead of the HNPP and 2-biphenyl diazonium chloride used in Example 1. In the reaction solution, the concentration of HNPP was 100 µg/ml, while that of the above Fast Red B (green) was 2.5 mg/ml.

Figure 16:
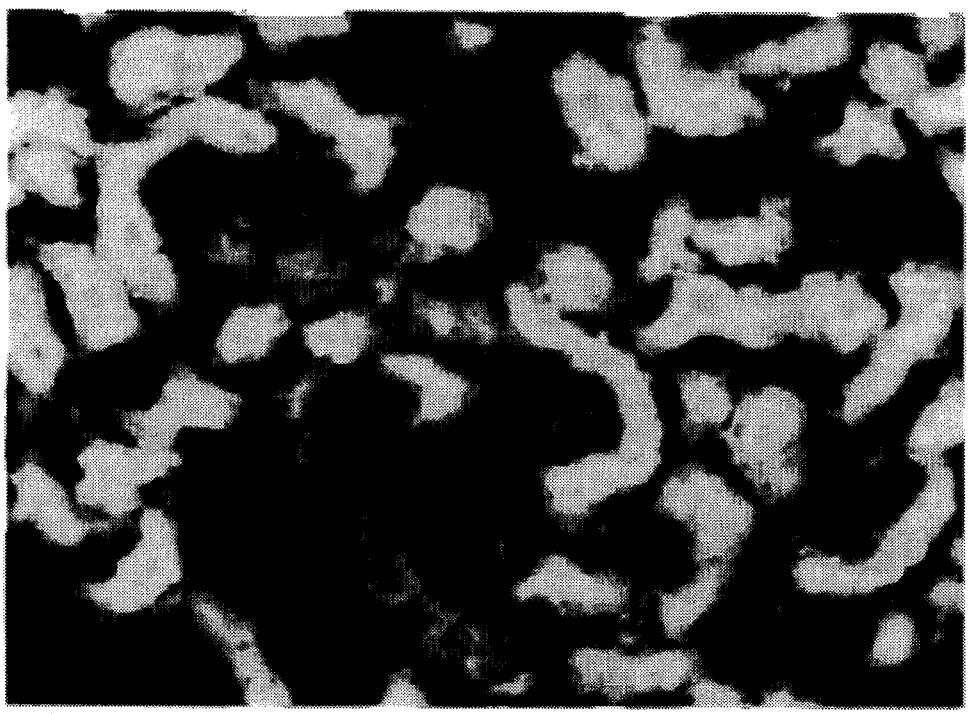
FIG. 16 is a photomicrograph (magnification:×100) of a mouse kidney tissue which shows the detection of phosphatase by the use of HNPP and a diazonium salt (Fast Red B (green)) in Example 3.

Otherwise, in the same manner as in Example 1, detection was made of phosphatase on a frozen tissue preparation from mouse kidneys. Observed fluorescent signal which was emitted from the tissue slice on a slide glass under a fluorescence microscope is shown in FIG. 16 (photograph, microscope magnification:×100; aperture: open, exposure time: 30 seconds) which demonstrates the detection of an intense yellow fluorescence.

Example 4

In this example, detection was made of a specific DNA sequence in a salivary chromosome sample from a yellow fruit-fly (in situ).

That is, a salivary gland was extracted from a third instar larva of *Drosophila melanogaster*, and spread on a slide glass, after which the sample DNA was subjected to alkali denaturation in a 0.07N NaOH solution. Next, it was hybridized with a part of GGPD (Glucose-6-Phosphate Dehydrogenase) gene sequence as the nucleic acid probe.

The nucleic acid probe was labelled with digoxigenin according to the random priming technique. After the hybridization followed by washing, blocking treatment was made with bovine serum albumin, after which, following the protocol of the Boehringer Mannheim AG, the alkali phosphatase-labelled anti-digoxigenin antibody was bound to the digoxigenin.

After the excess antibody was washed off, the above slide glass was immersed into the reaction solution which contained HNPP and Fast Red TR (4-chloro-2-methylbenzene diazonium chloride) (HNPP: 100 µm, Fast Red TR: 2.5 mg/ml), followed by a 2 hour reaction at 37° C. which produced a detectable red band on the chromosome.

Comparison 1

In this comparison, a substrate solution was prepared by using an equivolume of Naphthol AS-MX Phosphate (3-hydroxy-N-2',4'-dimethylphenylnaphthalenecarboxamide phosphate ester) instead of the HNPP in Example 1, and otherwise in the same manner as in Example, detection of phosphatase was made for a frozen tissue preparation from mouse kidneys.

Figure 17:
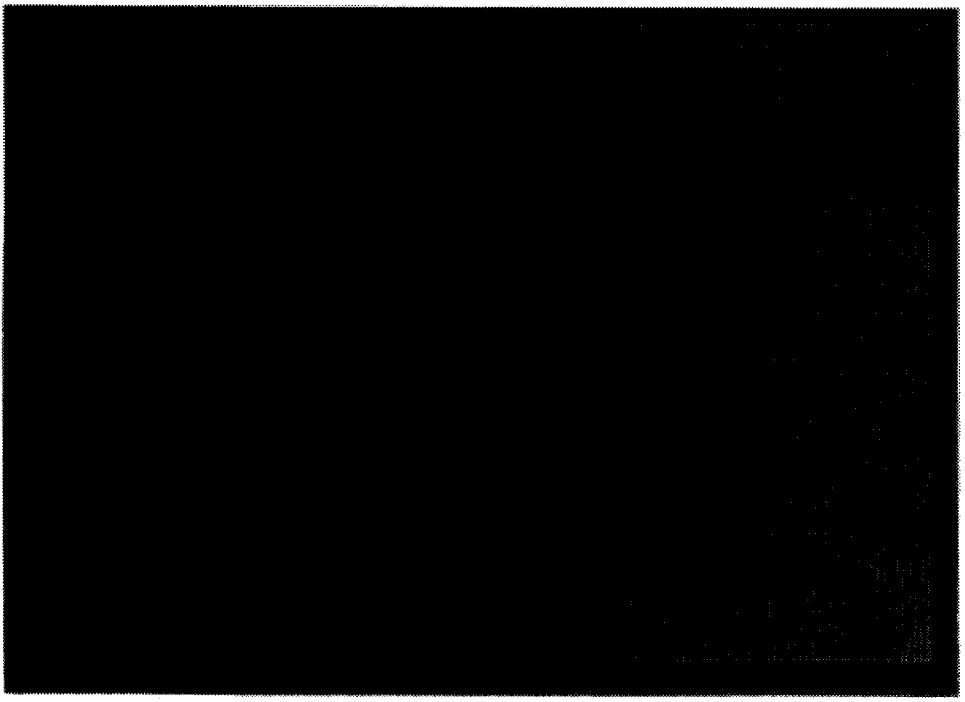
FIG. 17 is a photomicrograph (magnification:×100) of a mouse kidney tissue which shows the detection of phosphatase by the use of Naphthol AS/MX Phosphate and a diazonium salt (2-biphenyl diazonium chloride) in Comparison 1.

As is shown in FIG. 17, the result was that the fluorescent was significantly weak as compared with that in Example 1.

Comparison 2

In this comparison, a substrate solution was prepared by using a Naphthol AS-BI Phosphate (7-bromo-3-hydroxy-N-2'-methoxyphenylnaphthalenecarboxamide phosphate ester) instead of the HNPP in Example 1, and otherwise in the same manner as in Example 1, detection of phosphatase was made for a frozen tissue preparation from mouse kidneys. The result was the same as in Example 1 in that the fluorescent was significantly weak.

Example 5

In this example, 3-hydroxy-N-2'-biphenyl-2-naphthalenecarboxamide phosphate ester(HNPP) and 2-biphenyl diazonium chloride were synthesized and used for the detection of phosphatase in a frozen tissue preparation of mouse kidneys.

Hereunder the foregoing will be explained in detail.

1) Method for synthesis of HNPP

First, 18 g (0.1 mol) of 2-hydroxy-3-naphthoic acid, 200 ml of dehydrated xylene and 15 g (0.09 mol) of 2-amino biphenyl were charged into a 300 cc matrass equipped with a Dimroth condenser, and a mixture was stirred at 80° C. for 10 minutes.

Then phosphorus trichloride (0.03 mol) was added to the mixture which was then refluxed for 2 hours. Subsequently the reaction solution was decanted while hot to collect the supernatant. This supernatant was then cooled for precipitation. The resulting precipitate was filtered off, and washed with xylene and then with distilled water. This precipitate was then put in a 3% aqueous solution of hydrochloric acid, filtered after heating, after which the solution was cooled to separate a precipitate. After that, this precipitate was washed with hot water, and then dried.

Next, this precipitate was recrystallized to yield 3-hydroxy-N-2'-biphenyl-2-naphthalenecarboxamide represented by the formula V.

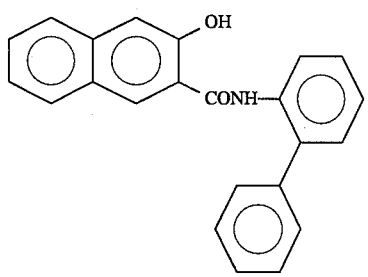

(V)

Then, 5.09 g (0.015 mol) portion of this 3-hydroxy-N-2'-biphenyl-2-naphthalenecarboxamide was dissolved in 200 ml of dioxane, and to the resulting solution there was added 15.6 g (0.075 mol) of phosphorus pentachloride, followed by stirring at 50° C. for 1 hour. Thereafter the mixture was slowly poured into 400 ml of icy water to separate crystals which were then filtered off.

Thereafter, the filtered-off crystals were well dried, and then dissolved in the minimal volume of N.N'-dimethylformamide. Next, the resulting solution was poured into a 0.2N sodium carbonate solution in water, which was then stirred at 0° C. for 2 hours without any further processing. Afterwards the crystals in the solution were removed by filtration by suction which was repeated twice. Next, a small cup receiving a 0.45 μm filtration paper (product of Millipore Co.) was used for additional filtration by suction, and 3N hydrochloric acid was added to the filtrate for recrystallization.

After that, the resulting suspension containing the crystals due to the recrystallization was subjected to filtration, well washed with distilled water and then dried to provide 1.4 g of HNPP (3-hydroxy-N-2'-biphenyl-2-naphthalenecarboxamide phosphate ester).

2) Method for synthesis of 2-biphenyl diazonium chloride

First, 500 mg of o-aminobiphenyl was suspended in 13.6% hydrochloric acid, and the resulting solution was subjected to ultrasonic treatment for 10 minutes and then kept at freezing point.

To the solution at freezing point was added 812 μl of a 25% aqueous solution of sodium nitrite, followed by stirring at 0° C. for 2 hours. Then, to the solution was added 600 μl of a saturated aqueous solution of zinc chloride while stirring, and the mixture was allowed to stand 0° C. for precipitation of crystals for 2 hours while stirring sometimes. Then filtration was carried out to separate the crystals which were then washed with cold ether and air-dried satisfactorily to yield 650 mg of zinc chloride double salt of 2-biphenyl diazonium chloride.

3) Preparation of reaction solution

Next, the above-mentioned HNPP and 2-biphenyl diazonium chloride were: dissolved in an HCl buffer solution at pH 8 to prepare a reaction solution. In this reaction solution, HNPP was present at $2.5 \times 10^{-4}$ mol/l, whereas 2-biphenyl diazonium chloride at $8.8 \times 10^{-4}$ mol/l.

4) Detection:of phosphatase on frozen tissue preparation from mouse kidneys

Next, kidneys were extracted from a mouse and was frozen at −15° C. to prepare a frozen tissue slice therefrom.

The slice was immersed into −15° C. for several or more hours, after which it was f i x ed on a slid glass in 4 % paraformamide at 4° C. for 20 minutes, and washed with a phosphate buffer solution on three times each for 5 minutes, and stored in a phosphate buffer solution at 4° C.

Afterwards the slide glass with the above-mentioned frozen tissue slice thereon was immersed into the above-mentioned reaction solution, followed by a reaction for approximately 5 minutes at room temperature. After the reaction, the slice was washed with water three times, well drained off, and thereafter encapsulated into glycerol.

Figure 18:
FIG. 18 is a photomicrograph (magnification:× 100) of a frozen mouse kidney tissue which shows the detection of phosphatase by the use of HNPP and 2-biphenyl diazonium chloride in Example 5.

Next, the observation of a fluorescent signal from the phosphatase in the frozen tissue slice was carried out with a fluorescence microscope to detect an intense red fluorescence as shown in FIG. 18.

For reference, the above result was compared with that of the commercially available Naphthol AS-MX Phosphate or Naphthol AS-BI Phosphate. As a result, the fluorescence of the former case was significantly weaker than that of the case of the use of HNPP, and the fluorescence was so much weaker in the latter case that it could not be detected.

Example 6

In this example, each of the diazonium salts listed below as 1)–8) was used, and alkaline phosphatase in a frozen tissue from mouse kidneys was detected in the same manner as in Example 5.

1) Fast Red TR (4-chloro-2-methylbenzene diazonium chloride);
2) Fast Red B (green) (2-methoxy-4-nitrobenzene diazonium chloride);
3) Fast Red GG (green) (4-nitrobenzene diazonium chloride);
4) Fast gordaux (;P (red) (4-methoxy-2-nitrobenzene diazonium chloride);
5) Fast Red ITR (green) (5-diethylaminosulfonyl-2-methoxybenzene diazonium chloride);
6) Naphthanil Diazo Red RC (red) (5-chloro-2-methoxybenzene diazonium chloride);
7) Naphthtalene diazonium salt; and
8) 3-methoxydibenzofuran diazonium salt.

As a result, an intense fluorescence was detected in each case in the same manner as in Example 5.

Example 7

In this example, detection was made of phosphatase on a frozen tissue preparation from mouse livers.

First, as in Example 5, HNPP and 2-biphenyl diazonium chloride were dissolved in a Tris-HCl buffer solution at pH 8 to prepare a reaction solution.

Separately, liver was extracted from a mouse and frozen with liquid nitrogen to prepare a frozen tissue slice. The slice was immersed into acetone at −70° C. overnight was then kept at 4° C.

Thereafter, the above-mentioned frozen tissue slice was immersed into 95 % ethanol, placed on a slide glass and then dried. Next, this slide glass was immersed into the above reaction solution for an approximately 5 minutes' reaction at 37° C. This:slide glass was washed with water after the reaction, then the slice was encapsulated into water.

Figure 19:
FIG. 19 is a photomicrograph (magnification:×100) of a frozen mouse liver tissue which shows the detection of phosphatase by the use of HNPP and 2-biphenyl diazonium chloride in Example 7.

Next, the observation of a fluorescent signal from the phosphatase in the frozen tissue slice was carried out by fluorescence microscopy; a strong red fluorescence was detected as shown in FIG. 19.

13

For reference the above-mentioned result was compared with the performance of the commercially available Naphthol AS-MX Phosphateor Naphthol AS-BI Phosphate. The fluorescence detected in the former case was remarkably weak as compared with the case of HNPP. The other case emitted an even weaker fluorescence which was hard to detect.

Example 8

In this example, detection was made of human satellite DNA (multicopy) on a human metaphase chromosome (detection of multicopy).

That is, first a metaphase chromosome specimen prepared from human peripheral blood lymphocytes was denatured by heating at 75° C. for 10 minutes.

Next, human satellite DNA was prepared by labelling with biotin according to the PCR, and hybridized (in situ) with the above-mentioned metaphase chromosome specimen as the nuclei acid probe. Thereafter, the above metaphase chromosome specimen hybridized with the above nucleic acid probe was washed.

Then, the metaphase chromosome specimen was subjected to a blocking treatment with an aqueous solution of dried skim milk for its linking with an alkali phosphatase-labelled anti-biotin antibody. After the excess antibody was removed, a 30 minutes' reaction was carried out in a reaction solution containing HNPP and 2-biphenyl diazonium chloride dissolved therein in an atmosphere at room temperature. The chromosome specimen underwent contrast staining with Hoechst-quinacrine.

Figure 20:
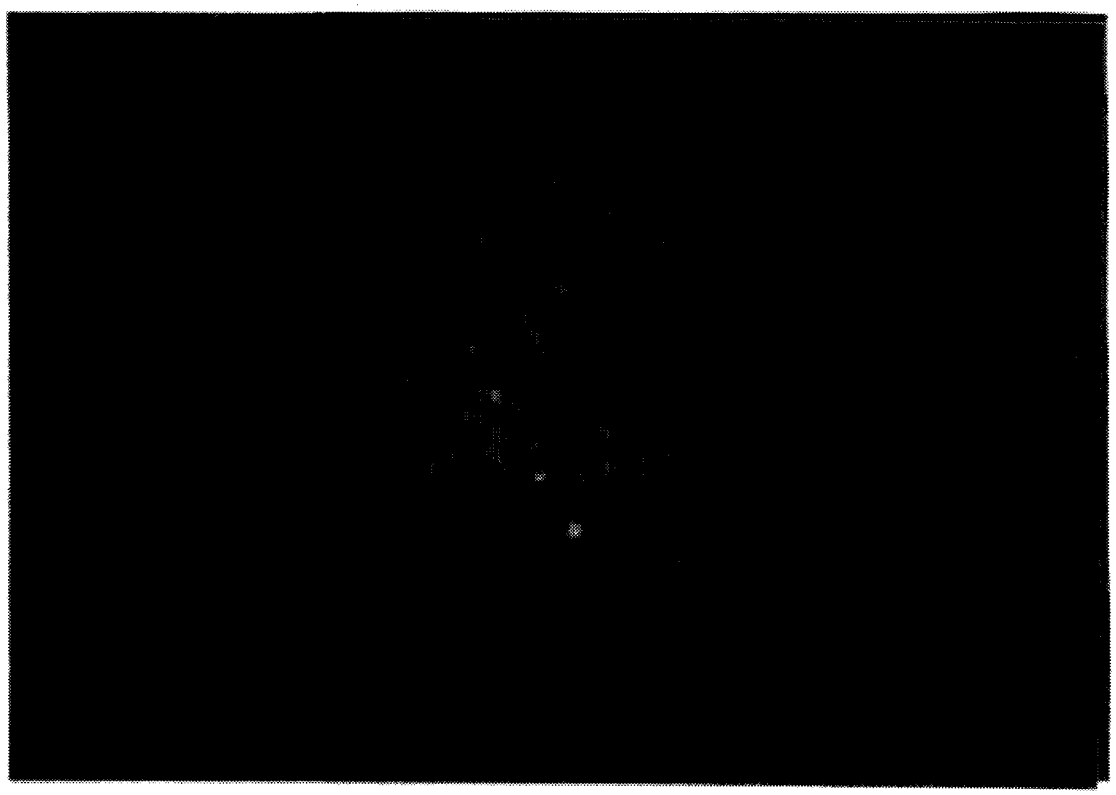
FIG. 20 is a photomicrograph (magnification:×100) of satellite DNA (multicopy) in a human metaphase chromosome which shows the detection of phosphatase by the use of HNPP and 2-biphenyl diazonium chloride in Example 8.

Subsequently, a fluorescence microscope was used for the observation of the above chromosome specimen. As a result, as shown in FIG. 20, an intense red fluorescent signal was detected in the centromere region of the chromosome. Also a vivid blue fluorescent band pattern of the chromosome was detected on the same photographed image.

Example 9

In this example, detection was made of human c-myc gene on a human chromosome specimen (detection of single copy).

That is, first a chromosome specimen prepared from human peripheral blood lymphocytes was denatured by heating at 75° C. for 10 minutes. Next, the human c-myc gene as the nucleic acid probe was labelled with biotin according to the nick-translation. After that, the labelled human c-myc gene was hybridized (in situ) with the above denatured chromosome specimen.

Then, the treatment was effected in the same manner as in Example 8, after which a 30 minutes' reaction was repeated four times in a reaction solution containing 100 µg/ml of HNPP and 250 µg/ml of 2-biphenyl diazonium chloride dissolved therein, at room temperature. The chromosome specimen underwent contrast staining with Hoechst-quinacrine.

Figure 21:
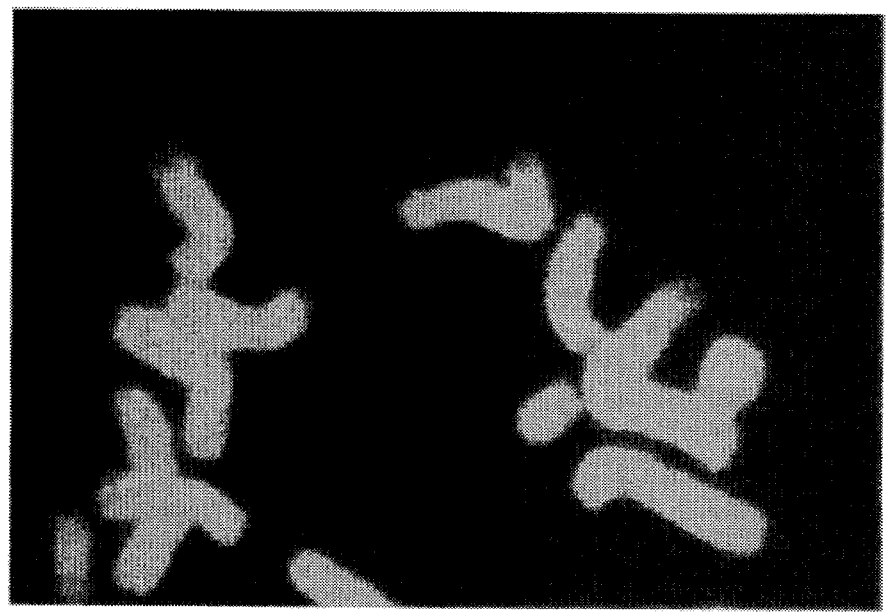
FIG. 21 is a photomicrograph (magnification:×100) of a single copy gene in a human chromosome (c-myc, cDNA, 2.4 kb) which shows the detection of phosphatase by the use of HNPP and 2-biphenyl diazonium chloride in Example 9.

Subsequently, a fluorescence microscope was used for the observation of the above chromosome specimen. As a result, as shown in FIG. 21, an intense red fluorescent signal was detected on the 8th chromosome. Also a vivid green fluorescent pattern of the entire chromosome was detected on the same photographed image.

Also in this example, a nucleic acid consisting of a short chain of 2.4 kb was hybridized with a certain base sequence site which was detected successfully.

14

Example 10

In this example, HMPNP (3-hydroxy-N-2'-methylphenyl-2-naphthalenecarboxamide phosphate ester) was synthesized, and with this the detection of phosphatase on a frozen tissue preparation from mouse kidneys was carried out in the same manner as in Example 5.

First, 5 g (0.027 mol) of 2-hydroxy-3-naphthoic acid, 40 ml of dehydrated xylene and 0.023 mol of 2-aminotoluene were charged into a 300 cc matrass equipped with a Dimroth condenser, and the mixture was stirred at 80° C. for 10 minutes.

Then phosphorus trichloride (0.01 mol) was added to the mixture. Then this mixture was refluxed for 2 hours. Subsequently the reaction solution was decanted while hot to collect the supernatant. This supernatant was then cooled to 4° C., and the separated precipitate was filtered off.

Thereafter the precipitate was washed with xylene and then with distilled water. This precipitate was then put in a 3% aqueous solution of hydrochloric acid, filtered after heating, after which the solution was cooled. The filtered-off precipitate was washed with hot water, and then dried. Next, this precipitate was recrystallized to yield 3-hydroxy-N-2'-methylphenyl-2naphthalenecarboxamide represented by the formula VI.

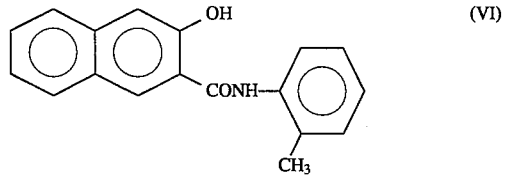

Then, 5 g (0.015 mol) portion of this 3-hydroxy-N-2'-methylphenyl-2-naphthalenecarboxamide was dissolved in 200 ml of dioxane, and to the resulting solution there was added 15.6 g (0.075 mol) of phosphorus pentachloride, followed by stirring at 50° C. for 1 hour. Thereafter the mixture was slowly poured into 400 ml of icy water to separate crystals which were then filtered off. Thereafter the crystals were well dried, and then dissolved in the minimal volume of N.N'-dimethylformamide. Next the resulting solution was poured into a 0.2N sodium carbonate solution in water, which was then stirred at 0° C. for 2 hours without any further processing.

Afterwards the crystals in the solution were removed by filtration by suction which was repeated twice. Next a small cup (product of Millipore Co.) was used for additional filtration by suction, and 3N hydrochloric acid was added to the filtrate for recrystallization.

After that, the resulting suspension containing crystals was subjected to filtration, well washed with distilled water and then dried. Thus there was provided 800 mg of 3-hydroxy-N-2'-methylphenyl-2-naphthalenecarboxamide phosphate ester.

Figure 22:
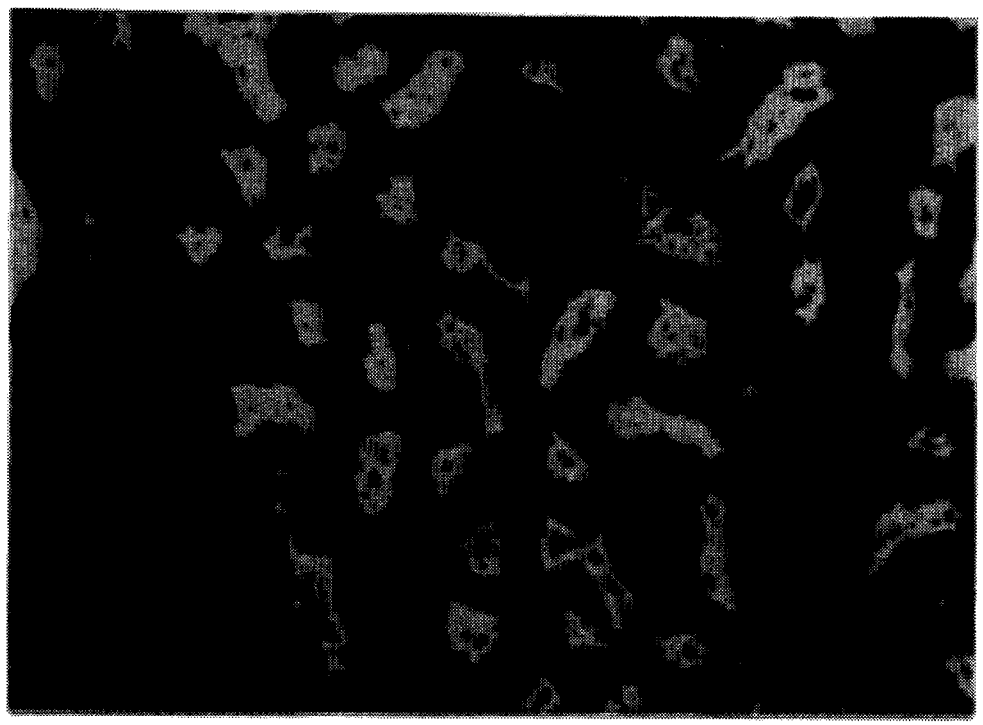
FIG. 22 is a photomicrograph (magnification:×100) of a frozen mouse kidney tissue which shows the detection of phosphatase by the use of HMPNP (3-hydroxy-N-2'-methylphenyl-2-naphthalenecarboxamide phosphate ester) and 2-biphenyl diazonium chloride in Example 10.

Next, with the: thus obtained 3-hydroxy-N-2'-methylphenyl-2-naphthalenecarboxamide phosphate ester was used, and alkaline phosphatase on a frozen tissue from mouse kidneys was detected in the same manner as in Example 5. As a result, as shown in FIG. 22, an intense red fluorescence was detected as the fluorescent signal from the phosphatase in a frozen tissue slice from mouse kidneys.

Example 11

In this example, 7-bromo-3-hydroxy-N-2'-biphenyl-2-naphthalenecarboxamide phosphate ester was synthesized, and with this the detection of phosphatase on a frozen tissue preparation from mouse kidneys was carried out in the same manner as in Example 5.

That is, first 5 g of cyanuric chloride was dissolved in 100 ml of acetone, followed by addition of 10 g o f Naphthol AS-BI (product of Sigm Co.) and then 24 ml of 10% caustic soda to the resulting solution which was further stirred for 3 hours. After that, 500 ml of 3% caustic soda was vigorously poured into the mixture which was stirred at 60° C. for 5 hours, followed by further stirring at room temperature overnight.

Then the solution was filtered, and the acetone in the filtrate was removed with an evaporator, after which conc. hydrochloric acid was added to the remaining solution. The precipitated crystals were extracted with ethyl acetate, dehydrated and then dried. Thus there was obtained 7-bromo-3-hydroxy-N-2-naphthalenecarboxylic acid.

Thereafter 5 g (0.027 mol) portion of this 7-bromo-3-hydroxy-N-2-naphthalenecarboxylic acid, 40 ml of dehydrated xylene and 0.023 mol of 2-aminobiphenyl were charged into a 100 ml matrass equipped with a Dimroth condenser, and the mixture was stirred at 80° C. for 10 minutes.

Then phosphorus trichloride (0.01 mol) was added to the mixture which was then refluxed for 2 hours. Subsequently the reaction solution was decanted while hot to collect the supernatant. This supernatant was then cooled to 4° C. for precipitation. The precipitate was filtered off, after which it was washed with xylene and then with distilled water. Next this precipitate was put in a 3% aqueous solution of hydrochloric acid, filtered after heating, and then the solution was cooled. Thereafter the precipitate was washed with hot water, and then dried.

Next, this precipitate was recrystallized to yield 7-bromo-3-hydroxy-N-2'-biphenyl-2-naphthalenecarboxamide represented by the formula VII.

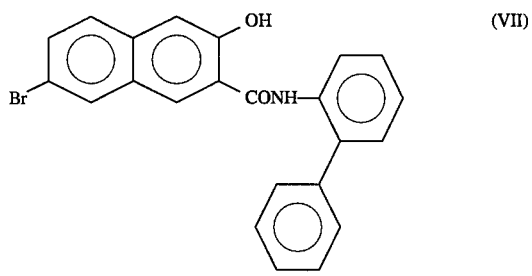

(VII)

Then 4 g (0.0mol) portion of this 7-bromo-3-hydroxy-N-2'-biphenyl-2-naphthalenecarboxamide was dissolved in 120 ml of dioxane, and t o the resulting solution there was added 11.26 g (0.05 mol) of phosphorus pentachloride, followed by stirring at 50° C. for 1 hour. Thereafter the mixture was slowly poured into 250 ml of icy water to separate crystals which were then filtered off. The crystals were well dried, and then dissolved in the minimal volume of N,N'-dimethyl-formamide.

Next the resulting solution was poured into a 0.2N sodium carbonate solution in water, which was then stirred at 0° C. for 2 hours without any further processing. Afterwards the crystals which precipitated during the stirring were filtered off, and 3N HCl was added to the filtrate for crystallization. After that, the resulting suspension was subjected to filtration, and the obtained crystals were washed with distilled water to be dried. Thus there was provided 1.19 g of 7-bromo-3-hydroxy-N-2'-biphenyl-2-naphthalenecarboxamide phosphate ester represented by the formula VIII.

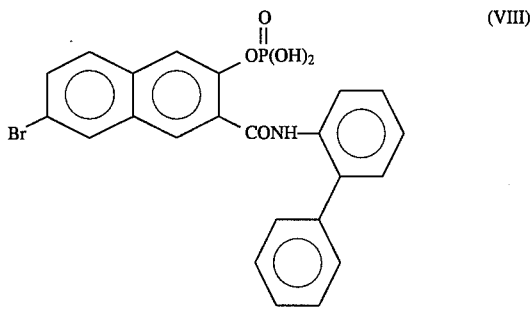

(VIII)

Next, with the thus obtained 7-bromo-3-hydroxy-N-2'-biphenyl-2-naphthalenecarboxamide phosphate ester, phosphatase on a frozen tissue preparation from mouse kidneys was detected in the same manner as in Example 5.

Figure 23:
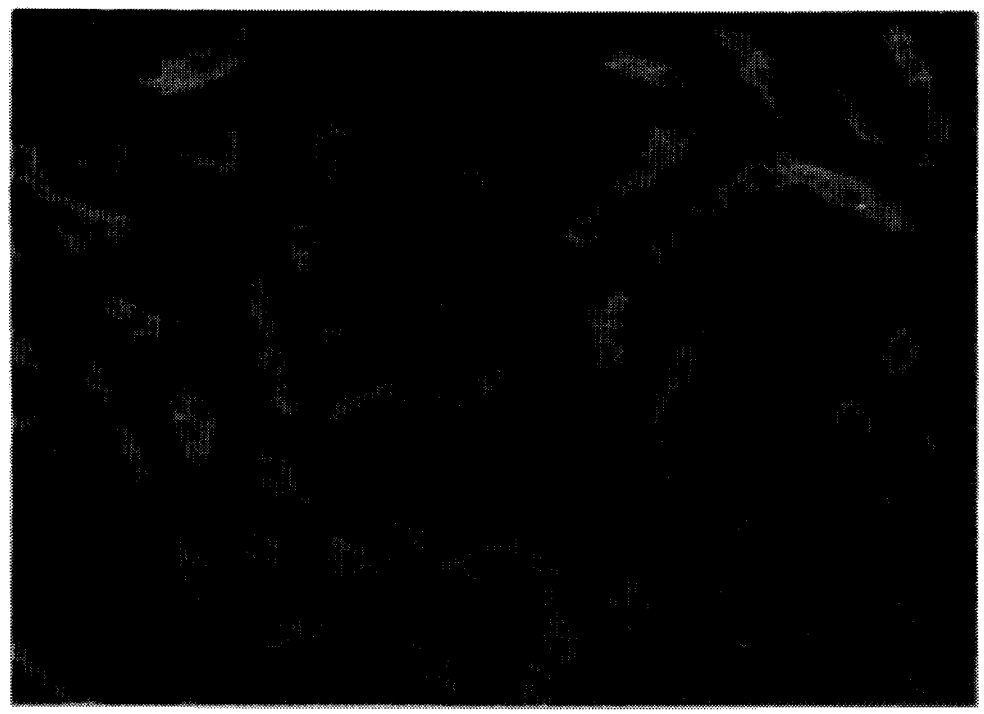
FIG. 23 is a photomicrograph (magnification:× 100) of a frozen mouse kidney tissue which shows the detection of phosphatase by the use of 7-bromo-3-hydroxy-N- 2'-biphenyl-2-naphthalenecarboxamide phosphate ester and 2-biphenyl diazonium chloride in Example 11.

As a result, as shown in FIG. 23, an intense red fluorescence was detected as the fluorescent signal from the phosphatase in a frozen tissue slice from mouse kidneys, which was the same as in Example 5.

Example 12

In this example, in the same manner as in Example 5, measurement was made of the degree of diffusion of phosphatase detected in a frozen mouse kidney tissue preparation, and the specific fluorescence intensity, exciting wavelength ($\lambda_{ex}$) and fluorescence wavelength ($\lambda_{em}$) for azo dyes.

Figure 24:
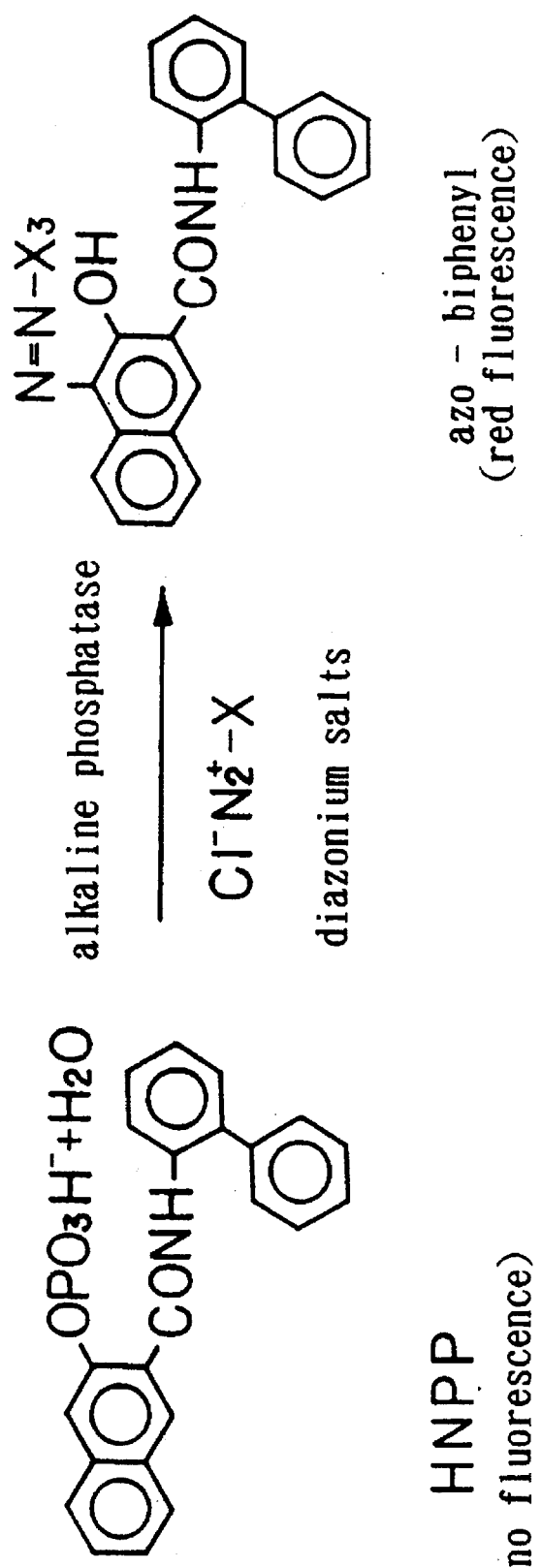
FIG. 24 illustrates the reactions between HNPP and a variety of diazonium salts in Example 12.

For this detection, as is shown in FIG. 24, HNPP or a 2'-naphthol AS phosphate was reacted with 2 kinds of diazonium salts (samples 1 and 2). These diazonium salts are monosubstituted at the 2-position of the benzene ring.

For comparison, the one wherein chlorine (Cl) was substituted for the hydrogen (H) at the 4-position of the benzene ring of a diazonium salt (sample 3), the one wherein the hydrogens at the 2- and 5-positions were replaced by $C_6H_5$ and $OCH_3$ (sample 4) and the one with the 2- and 4-hydrogens replaced by $CH_3$ and Br (sample 5) were measured in the same manner as mentioned above.

The results are shown in FIG. 25. In FIG. 25, $X_3$ is a benzene ring bound to the azo group in an azo dye and a side chain on the benzene ring, which is shown in FIG. 24. "Ph" stands for $C_6H_5$ (phenyl group). "$\lambda_{ex}$" stands for exciting wavelength. "$\lambda_{em}$" stands for fluorescence wavelength. "Specific FL" denotes relative fluorescence intensity as compared with sample 6 in Example 13 below for which 1 was assigned for the comparison with samples 1–5 in this example. Further "diffusion" stands for the diffusion of the fluorescent region of the tissue preparation; "Δ" for a moderate degree of diffusion, and "x" for a large degree of diffusion.

As the above-mentioned figure shows, such diazonium salts with phenyl or methyl group at the 2-position of the benzene ring as samples 1 and 2 according to the present invention provided a high specific FL and no diffusion. On the contrary, low specific FL and diffusion were observed for samples 3–5. These results teach that only 2-monosubstituted ones reflect satisfactory structures.

Example 13

In this example, in the same manner as in Example 10, measurement was made of the degree of diffusion of phosphatase detected in a frozen mouse kidney tissue preparation, and the exciting wavelength, fluorescence wavelength and relative fluorescence intensity for azo dyes.

Figure 26:
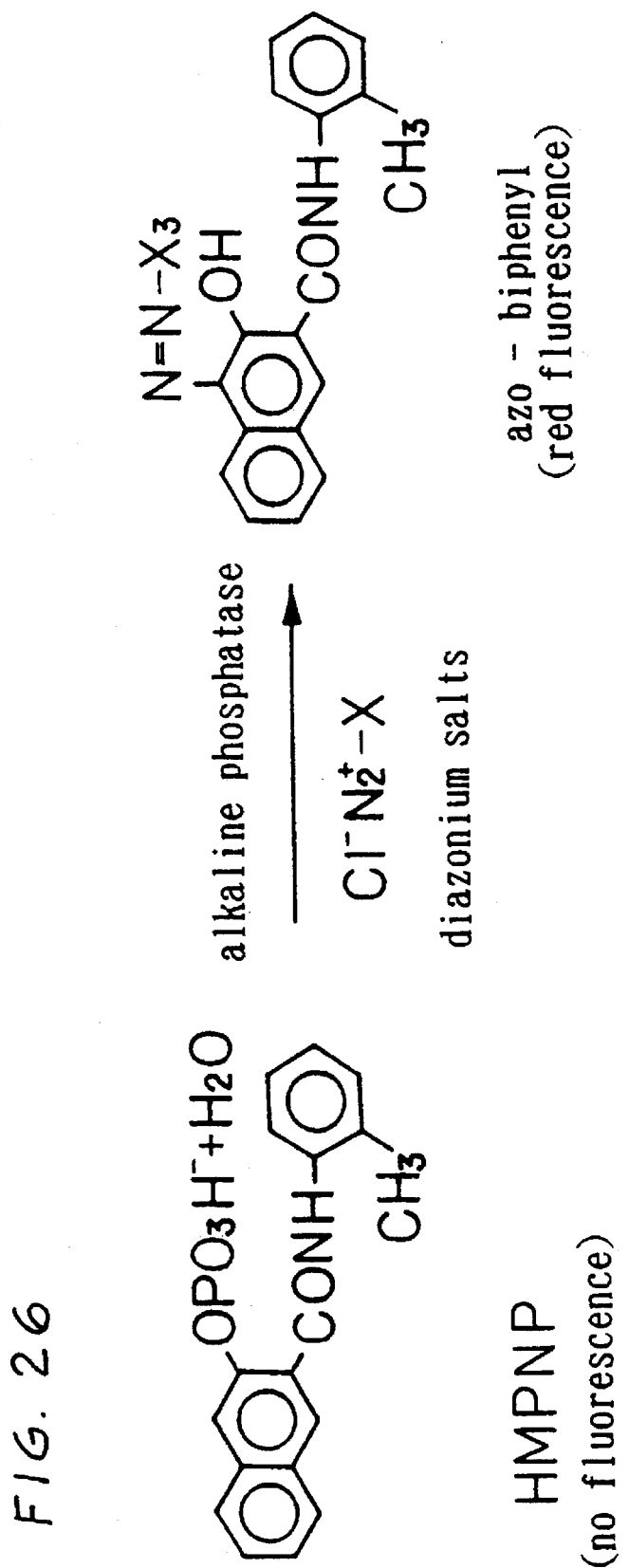
FIG. 26 illustrates the reactions between HMPNP and a variety of diazonium salts in Example 13.

For this detection, as is shown in FIG. 26, HMPNP or a 2'-naphthol AS phosphate was reacted with 2 kinds of diazonium salts (samples 6 and 7).

For comparison, the one wherein chlorine (Cl) was substituted for the hydrogen (H) at the 4-position of the benzene ring of a diazonium salt (sample 8), the one wherein the hydrogens at the 2- and 5-positions were replaced by $C_6H_5$ and $OCH_3$ (sample 9) and the one with the 2- and 4-hydrogens replaced by $CH_3$ and Br (sample 10) were measured in the same manner as mentioned above.

The results are shown in FIG. 27 similarly in FIG. 25 for Example 25. Here, regarding the "specific FL", 1 was assigned to sample 6 for the comparison with the other samples 7–10.

As the above-mentioned figure shows, such diazonium salts with phenyl or methyl group at the 2-position of the benzene ring as those according to the present invention caused little diffusion. On the contrary, rather great diffusion was observed for comparison samples 8–9. These results teach that only 2-monosubstituted ones reflect satisfactory structures.

What is claimed is:

1. A method for detecting the presence of phosphatase in a sample comprising the following steps:

(i) reacting a phosphatase contained in the sample with the 3-hydroxy-N-2'-biphenyl-2-naphthalenecarboxamide phosphate ester compound represented by the formula below:

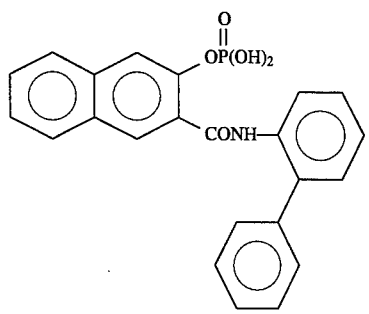

(ii) reacting the resultant dephosphorylated 3-hydroxy-N-2'-biphenyl-2-naphthalenecarboxamide phosphate-phosphatase reaction product with a diazonium salt represented by formulas below to produce an azo dye reaction product:

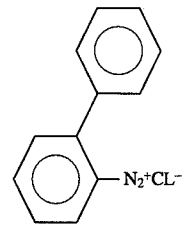

(2-Biphenyldiazonium chloride)

(iii) detecting emitted fluorescence of the azo-dye under irradiation of ultra-violet light to detect whether phosphatase is present in the sample.

2. The method of detecting phosphatase of claim 1 wherein the phosphatase containing sample is a tissue or cell.

3. The method of claim 2 wherein said phosphatase is attached to a nucleic acid probe.

4. The method of claim 3 wherein said probe is hybridized with RNA or DNA in a tissue or cell.

* * * * *